US012668755B2

(12) United States Patent
Tanji

(10) Patent No.: US 12,668,755 B2
(45) Date of Patent: Jun. 30, 2026

(54) FLUORINE-CONTAINING ETHER COMPOUND, LUBRICANT FOR MAGNETIC RECORDING MEDIUM AND MAGNETIC RECORDING MEDIUM

(71) Applicant: Resonac Corporation, Tokyo (JP)

(72) Inventor: Yutaka Tanji, Tokyo (JP)

(73) Assignee: Resonac Corporation, Tokyo (JP)

( * ) Notice: Subject to any disclaimer, the term of this patent is extended or adjusted under 35 U.S.C. 154(b) by 43 days.

(21) Appl. No.: 18/866,165

(22) PCT Filed: May 18, 2023

(86) PCT No.: PCT/JP2023/018608

§ 371 (c)(1),
(2) Date: Nov. 15, 2024

(87) PCT Pub. No.: WO2023/224095

PCT Pub. Date: Nov. 23, 2023

(65) Prior Publication Data

US 2025/0326980 A1 Oct. 23, 2025

(30) Foreign Application Priority Data

May 20, 2022 (JP) ................................ 2022-083154

(51) Int. Cl.
*C10M 105/54* (2006.01)
*C07C 43/12* (2006.01)
(Continued)

(52) U.S. Cl.
CPC ......... *C10M 105/54* (2013.01); *C07C 43/126* (2013.01); *G11B 5/708* (2013.01);
(Continued)

(58) Field of Classification Search
CPC ... C07C 233/18; C07C 255/20; C07C 43/126; C07C 43/137; C10M 105/54;
(Continued)

(56) References Cited

U.S. PATENT DOCUMENTS

2016/0260452 A1 9/2016 Pathem

FOREIGN PATENT DOCUMENTS

JP 5334064 B2 11/2013
JP 2021-123575 A 8/2021
(Continued)

*Primary Examiner* — Holly Rickman
*Assistant Examiner* — Linda N Chau
(74) *Attorney, Agent, or Firm* — Sughrue Mion, PLLC

(57) ABSTRACT

A fluorine-containing ether compound represented by the following formula: $R^1—R^2—CH_2—R^3[—CH_2—R^4—CH_2—R^3]_x—CH_2—R^5—R^6$ ($R^1$ and $R^6$ are an organic group having 1 to 50 carbon atoms; $R^2$ is Formula (2-1) or (2-2); $R^5$ is Formula (2-3) or (2-4); $R^3$ is a perfluoropolyether chain; $R^4$ is Formula (3-1) or (3-2); and x is 0 to 2).

[Chem. 1]

(2-1)

(2-2)

(2-3)

(2-4)

(3-1)

(Continued)

-continued

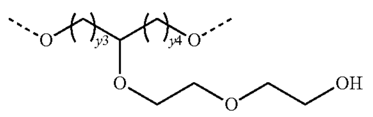

(3-2)

13 Claims, 1 Drawing Sheet

(51) Int. Cl.
*G11B 5/708* (2006.01)
*G11B 5/725* (2006.01)
*C10N 40/18* (2006.01)

(52) U.S. Cl.
CPC ... *G11B 5/7253* (2020.08); *C10M 2211/0425* (2013.01); *C10N 2040/18* (2013.01)

(58) Field of Classification Search
CPC ........ C10M 107/38; C10M 2211/0425; C10M 2213/043; C10N 2020/02; C10N 2040/18; C10N 2050/023; G11B 5/70; G11B 5/708; G11B 5/725; G11B 5/7253; G11B 5/7257
See application file for complete search history.

(56) References Cited

FOREIGN PATENT DOCUMENTS

| | | | |
|---|---|---|---|
| WO | 2009/013785 | A1 | 1/2009 |
| WO | 2017/154403 | A1 | 9/2017 |
| WO | 2021/019998 | A1 | 2/2021 |
| WO | 2021/131993 | A1 | 7/2021 |
| WO | 2021/157563 | A1 | 8/2021 |
| WO | 2021/251335 | A1 | 12/2021 |

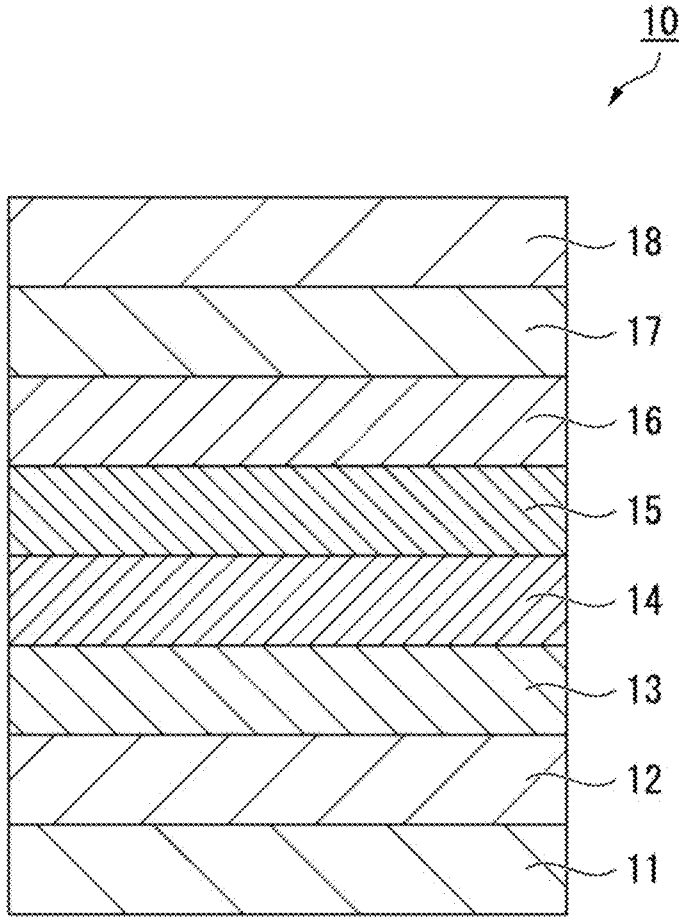
10
18
17
16
15
14
13
12
11

FLUORINE-CONTAINING ETHER COMPOUND, LUBRICANT FOR MAGNETIC RECORDING MEDIUM AND MAGNETIC RECORDING MEDIUM

TECHNICAL FIELD

The present invention relates to a fluorine-containing ether compound, a lubricant for magnetic recording medium and a magnetic recording medium.

This is a National Stage Application of International Application No. PCT/JP2023/018608 filed May 18, 2023, claiming priority based on Japanese Patent Application No. 2022-083154, filed May 20, 2022, the content of which is incorporated herein by reference.

BACKGROUND

The development of magnetic recording media suitable for high recording densities has progressed in order to improve the recording densities of magnetic recording and reproducing devices.

As a conventional magnetic recording medium, there has been a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, generally, a lubricant is applied to the surface of the protective layer to form a lubricating layer.

As a lubricant used when the lubricating layer of the magnetic recording medium is formed, for example, one containing a compound having a polar group such as a hydroxy group and an amino group at the terminal of a fluorine-based polymer having a repeating structure including $—CF_2—$ has been proposed.

For example, Patent Document 1 discloses a fluorine-containing ether compound in which a divalent linking group containing a secondary hydroxy group and a terminal group are bonded in this order at both terminals of a perfluoropolyether chain via a methylene group ($—CH_2—$).

In addition, Patent Document 2 discloses a fluorine-containing ether compound in which a glycerin structure ($—O—CH_2—CH(OH)—CH_2—O—$) is arranged in the center of a chain structure, and a perfluoropolyether chain, a divalent linking group containing a secondary hydroxy group, and a terminal group having a polar group are bonded in this order to both sides via a methylene group ($—CH_2—$).

In addition, Patent Document 3 discloses a fluorine-containing ether compound in which a perfluoropolyether chain and a terminal group are bonded in this order to both sides of a divalent linking group containing a primary hydroxy group and a secondary hydroxy group via a methylene group ($—CH_2—$).

In addition, Patent Document 4 discloses a fluorine-containing ether compound which has a framework in which three perfluoropolyether chains are bonded via a linking group containing a secondary hydroxy group and a divalent linking group containing a secondary hydroxy group and a terminal group having a polar group are bonded in this order to both sides via a methylene group ($—CH_2—$).

In addition, Patent Document 5 discloses a method of producing polyol(per)fluoropolyether derivatives useful as a lubricant for magnetic medium. Patent Document 5 describes that a protected triol having two protected hydroxy functional groups and one free hydroxy group is reacted with an activating agent to generate an activated protected triol, which is subjected to a nucleophilic substitution reaction with a hydroxy group arranged at the terminal of functional (per)fluoropolyether derivatives to generate protected polyol(per)fluoropolyether derivatives.

CITATION LIST

Patent Document

Patent Document 1: PCT International Publication No. WO2017/154403

Patent Document 2: PCT International Publication No. WO2021/251335

Patent Document 3: PCT International Publication No. WO2021/019998

Patent Document 4: U.S. Patent Application Publication No. 2016/0260452

Patent Document 5: Japanese Patent No. 5334064

SUMMARY OF INVENTION

Technical Problem

There is a demand for a further decrease in a raised amount of a magnetic head in magnetic recording and reproducing devices. This requires a further decrease in the thickness of a lubricating layer in magnetic recording media.

However, generally, when the thickness of the lubricating layer is reduced, the chemical substance resistance of magnetic recording media tends to decrease. In addition, when the raised amount of the magnetic head decreases, pickup in which the fluorine-containing ether compound in the lubricating layer adheres to the magnetic head may occur.

The present invention has been made in view of the above circumstances, and an object of the present invention is to provide a fluorine-containing ether compound which can form a lubricating layer that has excellent chemical substance resistance and can minimize the occurrence of pickup and can be suitably used as a material for a lubricant for magnetic recording medium.

In addition, an object of the present invention is to provide a lubricant for magnetic recording medium which contains the fluorine-containing ether compound of the present invention and can form a lubricating layer having favorable chemical substance resistance and a strong pickup minimizing effect.

In addition, an object of the present invention is to provide a magnetic recording medium which has a lubricating layer containing the fluorine-containing ether compound of the present invention and has favorable chemical substance resistance and a strong pickup minimizing effect.

Solution to Problem

The present invention includes the following aspects.

A first aspect of the present invention provides the following fluorine-containing ether compound.

[1] A fluorine-containing ether compound represented by the following Formula (1):

$$R^1—R^2—CH_2—R^3[—CH_2—R^4—CH_2—R^3]_x—CH_2—R^5—R^6 \qquad (1)$$

(in Formula (1), $R^1$ and $R^6$ are each independently an organic group having 1 to 50 carbon atoms; $R^2$ is a divalent linking group represented by the following Formula (2-1) or (2-2); $R^5$ is a divalent linking group represented by the following Formula (2-3) or (2-4); x represents an integer of 0 to 2; $R^3$ is a perfluoropolyether chain; when x is 1 or 2, some or all of two or three $R^3$'s may be the same as or different from each other; $R^4$ is a divalent linking group represented by the following Formula (3-1) or (3-2); and when x is 2, two $R^4$'s may be the same as or different from each other).

[Chem. 1]

(2-1)

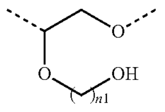

(2-2)

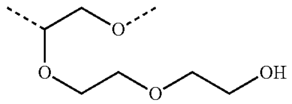

(2-3)

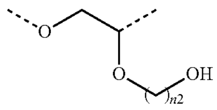

(2-4)

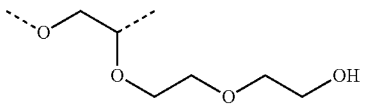

(3-1)

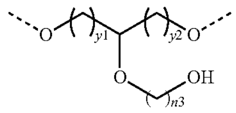

(3-2)

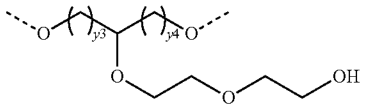

(in Formula (2-1), n1 represents an integer of 2 to 4; and in Formula (2-1), a dotted line bonded to a carbon atom indicates a bond that is bonded to $R^1$, and a dotted line bonded to an oxygen atom indicates a bond that is bonded to a methylene group) (in Formula (2-2), a dotted line bonded to a carbon atom indicates a bond that is bonded to $R^1$, and a dotted line bonded to an oxygen atom indicates a bond that is bonded to a methylene group) (in Formula (2-3), n2 represents an integer of 2 to 4; and in Formula (2-3), a dotted line bonded to a carbon atom indicates a bond that is bonded to $R^6$, and a dotted line bonded to an oxygen atom indicates a bond that is bonded to a methylene group) (in Formula (2-4), a dotted line bonded to a carbon atom indicates a bond that is bonded to $R^6$, and a dotted line bonded to an oxygen atom indicates a bond that is bonded to a methylene group)

(in Formula (3-1), n3 represents an integer of 2 to 4; y1 represents an integer of 1 to 3; y2 represents an integer of 1 to 3; at least one of y1 and y2 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$)

(in Formula (3-2), y3 represents an integer of 1 to 3; y4 represents an integer of 1 to 3; at least one of y3 and y4 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$).

The fluorine-containing ether compound according to the first aspect of the present invention preferably has features described in [2] to below. It is also preferable to arbitrarily combine two or more of the features described in [2] to below.

[2] The fluorine-containing ether compound according to [1], wherein, in Formula (1), $R^2$ is Formula (2-1) and $R^5$ is Formula (2-3), all x $R^4$'s are Formula (3-1), and in Formula (3-1), y1 is 1 and y2 is 1.

[3] The fluorine-containing ether compound according to [2], wherein the values of n1 in Formula (2-1), n2 in Formula (2-3) and n3 in Formula (3-1) are all the same.

[4] The fluorine-containing ether compound according to [1], wherein, in Formula (1), $R^2$ is Formula (2-2) and $R^5$ is Formula (2-4), all x $R^4$'s are Formula (3-2), and in Formula (3-2), y3 is 1 and y4 is 1.

[5] The fluorine-containing ether compound according to any one of [1] to [4], wherein, in Formula (1), $R^1$ and $R^6$ are each independently any of an organic group having a polar group, an organic group having a carbon-carbon unsaturated bond, and an organic group having both a polar group and a carbon-carbon unsaturated bond, wherein the polar group is at least one selected from the group consisting of a hydroxy group, an amino group, a carboxy group, a formyl group, a carbonyl group, a sulfo group, a cyano group, and a group having an amide bond, and wherein the carbon-carbon unsaturated bond is at least one selected from the group consisting of an optionally substituted aromatic hydrocarbon group, an unsaturated heterocyclic group, an alkenyl group, and an alkynyl group.

[6] The fluorine-containing ether compound according to any one of [1] to [5], wherein a total number of polar groups contained in $R^1$ and $R^6$ in Formula (1) is 1 to 4.

[7] The fluorine-containing ether compound according to any one of [1] to [6], wherein, in Formula (1), $R^1$—$R^2$— and $R^6$—$R^5$— are the same.

[8] The fluorine-containing ether compound according to any one of [1] to [7], wherein (x+1) $R^3$'s in Formula (1) are each independently a perfluoropolyether chain represented by the following Formula (4):

$$-(CF_2)_{w1}-O-(CF_2CF_2CF_2O)_{w2}-(CF_2CF_2O)_{w3}-(CF_2CF_2CF_2O)_{w4}-(CF_2CF_2CF_2CF_2O)_{w5}-(CF_2)_{w6}- \quad (4)$$

(in Formula (4), w2, w3, w4, and w5 indicate an average degree of polymerization and each independently represent 0 to 20; provided that all of w2, w3, w4, and w5 are not 0 at the same time; w1 and w6 are an average value representing the number of $CF_2$'s and each independently represent 1 to 3; and the arrangement order of repeating units $(CF_2O)$, $(CF_2CF_2O)$, $(CF_2CF_2CF_2O)$, and $(CF_2CF_2CF_2CF_2O)$ in Formula (4) is not particularly limited).

[9] The fluorine-containing ether compound according to any one of [1] to [7], wherein (x+1) $R^3$'s in Formula (1) are each independently any one selected from among perfluoropolyether chains represented by the following Formulae (4-1) to (4-4):

$$-CF_2-(OCF_2CF_2)_h-(OCF_2)_i-OCF_2- \quad (4\text{-}1)$$

(in Formula (4-1), h and i indicate an average degree of polymerization, h represents 1 to 20, and i represents 0 to 20)

$$-CF_2CF_2-(OCF_2CF_2CF_2)_j-OCF_2CF_2- \quad (4\text{-}2)$$

(in Formula (4-2), j indicates an average degree of polymerization and represents 1 to 15)

$$-CF_2CF_2CF_2-(OCF_2CF_2CF_2CF_2)_k-OCF_2CF_2CF_2- \quad (4\text{-}3)$$

(in Formula (4-3), k indicates an average degree of polymerization and represents 1 to 10)

$$-(CF_2)_{w7}-O-(CF_2CF_2CF_2O)_{w8}-(CF_2CF_2O)_{w9}-(CF_2)_{w10}- \quad (4\text{-}4)$$

(in Formula (4-4), w8 and w9 indicate an average degree of polymerization and each independently represent 1 to 20; w7 and w10 are an average value representing the number of $CF_2$'s and each independently represent 1 to 2).

[10] The fluorine-containing ether compound according to any one of [1] to [9], wherein the number-average molecular weight is in a range of 500 to 10,000.

A second aspect of the present invention provides the following lubricant for magnetic recording medium.

[11] A lubricant for magnetic recording medium including the fluorine-containing ether compound according to any one of [1] to [10].

A third aspect of the present invention provides the following magnetic recording medium.

[12] A magnetic recording medium in which at least a magnetic layer, a protective layer, and a lubricating layer are sequentially provided on a substrate, wherein the lubricating layer contains the fluorine-containing ether compound according to any one of [1] to [10].

The magnetic recording medium according to the third aspect of the present invention preferably has a feature described in below.

[13] The magnetic recording medium according to [12], wherein the average film thickness of the lubricating layer is 0.5 nm to 2.0 nm.

Advantageous Effects of Invention

The fluorine-containing ether compound of the present invention is the compound represented by Formula (1), and is suitable as a material for a lubricant for magnetic recording medium.

Since the lubricant for magnetic recording medium of the present invention contains the fluorine-containing ether compound of the present invention, it is possible to form a lubricating layer having favorable chemical substance resistance and a strong pickup minimizing effect.

The magnetic recording medium of the present invention has a lubricating layer containing the fluorine-containing ether compound of the present invention. Therefore, the magnetic recording medium of the present invention has favorable chemical substance resistance, a strong pickup minimizing effect, and excellent reliability and durability. In addition, since the lubricating layer of the magnetic recording medium of the present invention has favorable chemical substance resistance and can minimize the occurrence of pickup, it is possible to reduce the thickness and it is possible to reduce the raised amount of the magnetic head.

BRIEF DESCRIPTION OF DRAWINGS

The FIGURE is a schematic cross-sectional view showing a magnetic recording medium according to one embodiment of the present invention.

DESCRIPTION OF EMBODIMENTS

In order to achieve the above objects, the inventors conducted extensive studies as shown below.

In the related art, as a material for a lubricant for magnetic recording medium (hereinafter sometimes abbreviated as a "lubricant") applied to the surface of a protective layer, a fluorine-containing ether compound having a polar group such as a hydroxy group is preferably used. The polar groups in the fluorine-containing ether compound are bonded to the active sites on the protective layer to improve adhesion of the lubricating layer with respect to the protective layer. In conventional fluorine-containing ether compounds, polar groups are arranged at the terminals of the chain structure. In addition, when the fluorine-containing ether compound has a plurality of perfluoropolyether chains, a polar group is arranged between adjacent perfluoropolyether chains.

However, when a thin lubricating layer is formed on a protective layer using a conventional lubricant, it is difficult to realize a lubricating layer having favorable chemical substance resistance and a strong pickup minimizing effect.

The reason for this is, for example, the presence of polar groups in the fluorine-containing ether compound contained in the lubricating layer, which are not adsorbed to a plurality of active sites present on the protective layer.

When there are polar groups that are not adsorbed to the active sites on the protective layer in the fluorine-containing ether compound contained in the lubricating layer, contamination substances are likely to be taken in near the polar groups, and the chemical substance resistance of the lubricating layer decreases. In addition, the polar groups in the fluorine-containing ether compound, which are not adsorbed to the active sites on the protective layer, may be adsorbed to a magnetic head, and the fluorine-containing ether compound may be picked up by the magnetic head using them as starting points. Accordingly, when there are polar groups that not adsorbed to the active sites on the protective layer in the fluorine-containing ether compound contained in the lubricating layer, the chemical substance resistance and pickup minimizing effect of the lubricating layer are likely to be insufficient.

Thus, the inventors conducted extensive studies in order to realize a fluorine-containing ether compound in which polar groups that do not participate in bonding with the active sites on the protective layer are less likely to be generated, focusing on the behavior of bonding between the polar groups contained in the fluorine-containing ether compound and the active sites on the protective layer.

As a result, the inventors found that, among polar groups contained in the fluorine-containing ether compound, secondary hydroxy groups contained in the divalent linking group arranged between adjacent perfluoropolyether chains and between the perfluoropolyether chain and the terminal group are less likely to participate in bonding with the active sites on the protective layer.

Therefore, the inventors converted secondary hydroxy groups contained in the divalent linking group arranged between adjacent perfluoropolyether chains, and between the perfluoropolyether chain and the terminal group of the fluorine-containing ether compound into primary hydroxy groups by chemical modification. Then, a lubricating layer was formed using the converted fluorine-containing ether compound. As a result, it was found that the chemical substance resistance and the pickup minimizing effect were improved. This was speculated to be because a fluorine-containing ether compound in which hydroxy groups that are not bonded to the active sites present on the protective layer are less likely to be generated was obtained.

In addition, the inventors conducted extensive studies and found that it is sufficient to use a fluorine-containing ether compound in which a specific divalent terminal linking group having only one primary hydroxy group is arranged between a perfluoropolyether chain and a terminal group, and when two or three perfluoropolyether chains are provided, a specific divalent intermediate linking group having only one primary hydroxy group is arranged between the adjacent perfluoropolyether chains. Two terminal linking groups (two terminal linking groups and one or two intermediate linking groups when there are a plurality of perfluoropolyether chains) each have a side chain moiety branching from the chain structure of the fluorine-containing ether compound and are linked by an ether bond. The side chain moiety has a primary hydroxy group arranged at the tip and has a linking group containing a methylene group ($—CH_2—$) that bonds a carbon atom to which a primary hydroxy group is bonded and an oxygen atom that is bonded to a carbon atom in the chain structure.

In such a fluorine-containing ether compound, for the following reason, polar groups that are not bonded to functional groups (active sites) present on the protective layer are less likely to be generated. Therefore, it is speculated that a fluorine-containing ether compound which can form a lubricating layer having excellent chemical substance resistance and a strong pickup minimizing effect is obtained That is, the two terminal linking groups (the two terminal linking groups and one or two intermediate linking groups when there are a plurality of perfluoropolyether chains) each have only one primary hydroxy group, and are sterically vacant compared to when they have a secondary hydroxy group in place of the primary hydroxy group. Therefore, the primary hydroxy groups of the two terminal linking groups (or the two terminal linking groups and one or two intermediate linking groups) are less likely to be inhibited from bonding to the active sites on the protective layer due to bulky portions in the fluorine-containing ether compound such as adjacent perfluoropolyether chains and tertiary carbon to which a side chain moiety of each terminal linking group (or the two terminal linking groups and one or two intermediate linking groups) is bonded. Furthermore, the primary hydroxy group can generally move more freely than the secondary hydroxy group. Therefore, the primary hydroxy groups of the two terminal linking groups (or the two terminal linking groups and one or two intermediate linking groups) can each move spontaneously to the active sites on the protective layer. Accordingly, the primary hydroxy groups of the two terminal linking groups (or the two terminal linking groups and one or two intermediate linking groups) can easily form bonds with the active sites on the protective layer.

In addition, in the fluorine-containing ether compound, terminal linking groups are arranged between both terminal groups and the perfluoropolyether chain. Therefore, the distance between the primary hydroxy group of the terminal linking group arranged on one end side of the chain structure and the primary hydroxy group of the terminal linking group arranged on the other end side of the chain structure does not become too short. In addition, when the fluorine-containing ether compound has a plurality of perfluoropolyether chains, each perfluoropolyether chain is arranged between each of the terminal linking groups and one or two intermediate linking groups. Therefore, the distance between the primary hydroxy group of each terminal linking group and the primary hydroxy group of one or two intermediate linking groups does not become too short. In addition, when the fluorine-containing ether compound has three perfluoropolyether chains, two intermediate linking groups are present. In this case, since the perfluoropolyether chains are arranged between adjacent intermediate linking groups, the distance between the primary hydroxy groups of the adjacent intermediate linking groups does not become too short.

Therefore, in the fluorine-containing ether compound, the primary hydroxy groups of the two terminal linking groups (the two terminal linking groups and one or two intermediate linking groups when there are a plurality of perfluoropolyether chains) are less likely to be inhibited from bonding to the active sites on the protective layer due to the primary hydroxy group of other terminal linking groups (or other terminal linking groups and intermediate linking groups) contained in the fluorine-containing ether compound. In addition, in the fluorine-containing ether compound, the distances between the primary hydroxy groups of two terminal linking groups (or the distance between the primary hydroxy groups of the terminal linking groups, the distance between the primary hydroxy group of the terminal linking groups and the primary hydroxy group of one or two intermediate linking groups, and the distance between the primary hydroxy groups of adjacent intermediate linking groups) do not become too short. Therefore, the primary hydroxy groups of the two terminal linking groups (or the terminal linking groups and one or two intermediate linking groups) are unlikely to aggregate with each other.

In addition, in the fluorine-containing ether compound, the two terminal linking groups (or the two terminal linking groups and one or two intermediate linking groups) have only one primary hydroxy group, and a side chain moiety branching from the chain structure of the fluorine-containing ether compound and are linked by an ether bond. In the fluorine-containing ether compound, since the side chain moieties of two terminal linking groups (or the two terminal linking groups and one or two intermediate linking groups) branch from the chain structure and are linked by an ether bond, the flexibility of the side chain moiety is better compared to when the side chain moiety is directly bonded to the chain structure (bonded via a carbon-carbon bond). Therefore, the primary hydroxy groups of the side chain moieties of the two terminal linking groups (or the two terminal linking groups and one or two intermediate linking groups) can easily form bonds with the active sites on the protective layer.

In addition, in the fluorine-containing ether compound, in the side chain moieties of the two terminal linking groups (or the two terminal linking groups and one or two intermediate linking groups), a carbon atom to which a primary hydroxy group arranged at the tip is bonded and an oxygen atom that is bonded to a carbon atom in the chain structure are bonded by a linking group containing a methylene group ($—CH_2—$). Therefore, even if the terminal group contains a polar group, the distance between the polar group of the terminal group and the primary hydroxy group of the terminal linking group adjacent to the terminal group becomes appropriate. As a result, the primary hydroxy groups of the terminal linking groups are less likely to be inhibited from bonding to the active sites on the protective layer due to the polar group of the terminal group. In addition, since the distance between the primary hydroxy group of the terminal linking group and the polar group of the terminal group is appropriate, even if the terminal group contains a polar group, the primary hydroxy group of the terminal linking group adjacent to the terminal group and the polar group of the terminal group are unlikely to aggregate.

As described above, in the fluorine-containing ether compound, the flexibility of the side chain moieties of the two terminal linking groups (or the two terminal linking groups and one or two intermediate linking groups) is favorable, the primary hydroxy groups of the side chain moieties can move spontaneously and are unlikely to aggregate, and less likely to be inhibited from bonding to the active sites on the protective layer due to primary hydroxy groups of other terminal linking groups (or other terminal linking groups and intermediate linking groups), polar groups of the terminal groups, and bulky portions in the fluorine-containing ether compound. Accordingly, in the fluorine-containing ether compound, polar groups that are not bonded to functional groups (active sites) present on the protective layer are less likely to be generated. As a result, it is speculated that the fluorine-containing ether compound can form a lubricating layer which is unlikely to take in contamination substances, has favorable chemical substance resistance, is unlikely to be picked up by a magnetic head, and has a strong pickup minimizing effect.

In addition, the inventors confirmed that, when a lubricant containing the fluorine-containing ether compound is used, it is possible to form a lubricating layer having favorable chemical substance resistance and a strong pickup minimizing effect, and completed the present invention.

Hereinafter, preferable examples of a fluorine-containing ether compound, a lubricant for magnetic recording medium and a magnetic recording medium of the present invention will be described in detail. Here, the present invention is not limited to the following embodiments. In the present invention, numbers, amounts, positions, ratios, materials, configurations and the like can be added, omitted, substituted, and changed without departing from the spirit and scope of the present invention.

[Fluorine-Containing Ether Compound]

The fluorine-containing ether compound of the present embodiment is represented by the following Formula (1).

$$R^1—R^2—CH_2—R^3[—CH_2—R^4—CH_2—R^3]_x-CH_2—R^5—R^6 \quad (1)$$

(in Formula (1), $R^1$ and $R^6$ are each independently an organic group having 1 to 50 carbon atoms; $R^2$ is a divalent linking group represented by the following Formula (2-1) or (2-2); $R^5$ is a divalent linking group represented by the following Formula (2-3) or (2-4); x represents an integer of 0 to 2; $R^3$ is a perfluoropolyether chain; when x is 1 or 2, some or all of two or three $R^3$'s may be the same as or different from each other; $R^4$ is a divalent linking group represented by the following Formula (3-1) or (3-2); and when x is 2, two $R^4$'s may be the same as or different from each other).

[Chem. 2]

(2-1)

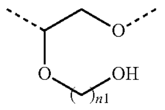

(2-2)

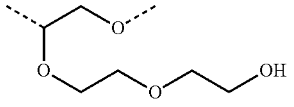

(in Formula (2-1), n1 represents an integer of 2 to 4; and in Formula (2-1), a dotted line bonded to a carbon atom indicates a bond that is bonded to $R^1$, and a dotted line bonded to an oxygen atom indicates a bond that is bonded to a methylene group) (in Formula (2-2), a dotted line bonded to a carbon atom indicates a bond that is bonded to $R^1$, and a dotted line bonded to an oxygen atom indicates a bond that is bonded to a methylene group).

[Chem. 3]

(2-3)

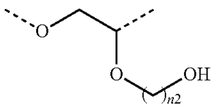

(2-4)

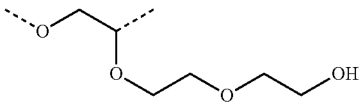

(in Formula (2-3), n2 represents an integer of 2 to 4; and in Formula (2-3), a dotted line bonded to a carbon atom indicates a bond that is bonded to $R^6$, and a dotted line bonded to an oxygen atom indicates a bond that is bonded to a methylene group) (in Formula (2-4), a dotted line bonded to a carbon atom indicates a bond that is bonded to $R^6$, and a dotted line bonded to an oxygen atom indicates a bond that is bonded to a methylene group).

[Chem. 4]

(3-1)

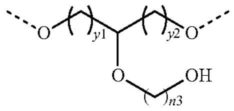

(3-2)

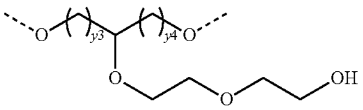

(in Formula (3-1), n3 represents an integer of 2 to 4; y1 represents an integer of 1 to 3; y2 represents an integer of 1 to 3; at least one of y1 and y2 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$).

(in Formula (3-2), y3 represents an integer of 1 to 3; y4 represents an integer of 1 to 3; at least one of y3 and y4 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$).

As shown in Formula (1), the fluorine-containing ether compound of the present embodiment has a chain structure framework in which a divalent terminal linking group having only one primary hydroxy group and represented by $R^2$, one to three perfluoropolyether chains represented by $R^3$ (hereinafter sometimes referred to as PFPE chains), 0 to 2 divalent intermediate linking groups having only one primary hydroxy group and represented by $R^4$, and a divalent terminal linking group having only one primary hydroxy group and represented by $R^5$ are linked via a methylene group. Terminal groups composed of organic groups having 1 to 50 carbon atoms and represented by $R^1$ and $R^6$ are bonded to both ends of the framework.

In the fluorine-containing ether compound represented by Formula (1), x represents an integer of 0 to 2. In the fluorine-containing ether compound represented by Formula (1), since x is 2 or less, the molecules do not become too large. Therefore, the fluorine-containing ether compound which can move freely on the protective layer, easily wets and spreads on the protective layer, and allows a lubricating layer having a uniform film thickness to be easily obtained is obtained. In addition, in order to obtain a fluorine-containing ether compound which can form a lubricating layer having better chemical substance resistance and a stronger pickup minimizing effect, x is preferably 1 or 2.

(Divalent Terminal Linking Group Having Only One Primary Hydroxy Group Represented by $R^2$ and $R^5$)

In the fluorine-containing ether compound represented by Formula (1), $R^2$ and $R^5$ are divalent terminal linking groups having only one primary hydroxy group. In the fluorine-containing ether compound represented by Formula (1), $R^2$ and $R^5$ each have no secondary hydroxy group, and have only one primary hydroxy group. Therefore, compared to when $R^2$ and $R^5$ each have a secondary hydroxy group, the hydroxy groups contained in $R^2$ and $R^5$ easily interact with the active sites on the protective layer. Therefore, when a lubricating layer is formed on the protective layer using the lubricant containing the fluorine-containing ether compound represented by Formula (1), a suitable interaction occurs between the lubricating layer and the protective layer. Therefore, the fluorine-containing ether compound represented by Formula (1) can form a lubricating layer having excellent chemical substance resistance and a strong pickup minimizing effect.

$R^2$ is a divalent linking group represented by Formula (2-1) or (2-2). The terminal of $R^2$ on the side of $R^3$ is an oxygen atom. The terminal of $R^2$ on the side of $R^3$ is bonded to a methylene group that is bonded to $R^3$ via an ether bond. The terminal of $R^2$ on the side of $R^1$ is a carbon atom. The terminal of the $R^2$ on the side of $R^1$ is bonded to $R^1$.

$R^2$ has a main chain moiety that forms the chain structure of the fluorine-containing ether compound and a side chain moiety branching from the main chain moiety at the carbon atom arranged at the terminal of the $R^2$ on the side of $R^1$ and linked by an ether bond. The side chain moiety has a primary hydroxy group arranged at the tip and has a linking group containing a methylene group ($—CH_2—$) that bonds a carbon atom to which a primary hydroxy group is bonded and an oxygen atom (etheric oxygen atom) that is bonded to a carbon atom in the main chain moiety.

$—(CH_2)_{n1}OH$ in Formula (2-1) or $—CH_2CH_2OCH_2CH_2OH$ in Formula (2-2) is bonded to the carbon atom arranged at the terminal of the $R^2$ on the side of $R^1$, as a side chain moiety, via an ether bond contained in $R^2$. In the present embodiment, when the side chain moiety for $R^2$ is ether-bonded to the carbon atom arranged at the terminal of the $R^2$ on the side of $R^1$, the side chain moiety for $R^2$ has better flexibility compared to when the side chain moiety for $R^2$ is directly bonded (bonded via a carbon-carbon bond) to the carbon atom arranged at the terminal of the $R^2$ on the side of $R^1$. Furthermore, in the present embodiment, the side chain moiety for $R^2$ has a chain structure containing a linking group and having an appropriate length. Therefore, the side chain moiety for $R^2$ easily interacts with the active sites on the protective layer.

In Formula (2-1), n1 is an integer of 2 to 4. When n1 is 2 or more, the distance between the primary hydroxy group contained in $R^2$ and a bulky portion such as the PFPE chain in the fluorine-containing ether compound or tertiary carbon arranged at the terminal of the $R^2$ on the side of $R^1$ becomes sufficiently long, and the primary hydroxy group contained in $R^2$ can easily freely move. In addition, when n1 is 4 or less, the flexibility of $—(CH_2)_{n1}OH$ in Formula (2-1) is maintained. n1 is preferably 2 to 3 and most preferably 2 because $—(CH_2)_{n1}OH$ can flexibly move.

In Formula (2-2), $—CH_2CH_2OCH_2CH_2OH$ contains an ether bond (—O—). Therefore, $—CH_2CH_2OCH_2CH_2OH$ in Formula (2-2) maintains flexibility of movement.

$R^5$ is a divalent linking group represented by Formula (2-3) or (2-4). The terminal of $R^5$ on the side of $R^3$ is an oxygen atom. The terminal of $R^5$ on the side of $R^3$ is bonded to a methylene group that is bonded to $R^3$ via an ether bond. The terminal of $R^5$ on the side of $R^6$ is a carbon atom. The terminal of the $R^5$ on the side of $R^6$ is bonded to $R^6$.

$R^5$ has a main chain moiety that forms the chain structure of the fluorine-containing ether compound and a side chain moiety branching from the main chain moiety at the carbon atom arranged at the terminal of the $R^5$ on the side of $R^6$ and linked by an ether bond. Similar to $R^2$, the side chain moiety has a primary hydroxy group arranged at the tip and has a linking group containing a methylene group ($—CH_2—$) that bonds a carbon atom to which a primary hydroxy group is bonded and an oxygen atom (etheric oxygen atom) that is bonded to a carbon atom in the main chain moiety.

$—(CH_2)_{n2}OH$ in Formula (2-3) or $—CH_2CH_2OCH_2CH_2OH$ in Formula (2-4) is bonded to the carbon atom arranged at the terminal of the $R^5$ on the side of $R^6$, as a side chain moiety, via an ether bond contained in $R^5$. In the present embodiment, when the side chain moiety for $R^5$ is ether-bonded to the carbon atom arranged at the terminal of the $R^5$ on the side of $R^6$, the side chain moiety for $R^5$ has better flexibility compared to when the side chain moiety for $R^5$ is directly bonded (bonded via a carbon-carbon bond) to the carbon atom arranged at the terminal of the $R^5$ on the side of $R^6$. Furthermore, in the present embodiment, the side chain moiety for $R^5$ has a chain structure containing a linking group and having an appropriate length. Therefore, the side chain moiety for $R^5$ easily interacts with the active sites on the protective layer.

In Formula (2-3), n2 is an integer of 2 to 4. When n2 is 2 or more, the distance between the primary hydroxy group contained in $R^5$ and a bulky portion such as the PFPE chain in the fluorine-containing ether compound or tertiary carbon arranged at the terminal of the $R^5$ on the side of $R^6$ becomes sufficiently long, and the primary hydroxy group contained in $R^5$ can easily freely move. In addition, when n2 is 4 or less, the flexibility of $—(CH_2)_{n1}OH$ in Formula (2-3) is maintained. n2 is preferably 2 to 3 and most preferably 2 because $—(CH_2)_{n2}OH$ can flexibly move.

In Formula (2-4), $—CH_2CH_2OCH_2CH_2OH$ contains an ether bond (—O—). Therefore, $—CH_2CH_2OCH_2CH_2OH$ in Formula (2-4) maintains flexibility of movement.

$R^2$ and $R^5$ may be the same as or different from each other. When $R^2$ and $R^5$ are the same, this is preferable because a fluorine-containing ether compound that is easy to produce is obtained.

In this specification, "$R^2$ and $R^5$ are the same" means that atoms contained in $R^2$ and atoms contained in $R^5$ are arranged symmetrically with respect to the structure represented by $—CH_2—R^3[—CH_2—R^4—CH_2—R^3]_x—CH_2—$ arranged in the center of the fluorine-containing ether compound represented by Formula (1).

That is, the fluorine-containing ether compound represented by Formula (1) is preferably a fluorine-containing ether compound in which $R^2$ is Formula (2-1), $R^5$ is Formula (2-3), and n1 in Formula (2-1) and n2 in Formula (2-3) are the same or a fluorine-containing ether compound in which $R^2$ is Formula (2-2) and $R^5$ is Formula (2-4).

(Divalent Intermediate Linking Group Having Only One Primary Hydroxy Group Represented by $R^4$)

In the fluorine-containing ether compound represented by Formula (1), when x is 1 or 2, PFPE chains represented by $R^3$ are bonded to each other via-$CH_2—R^4—CH_2—$. When x is 1 or 2, x $R^4$'s are divalent intermediate linking groups having only one primary hydroxy group. In the fluorine-containing ether compound represented by Formula (1), x $R^4$'s each have no secondary hydroxy group and have only one primary hydroxy group. Therefore, compared to when x $R^4$'s each have a secondary hydroxy group, the hydroxy groups contained in $R^4$ easily interact with the active sites on the protective layer. Therefore, when a lubricating layer is formed on the protective layer using the lubricant containing the fluorine-containing ether compound represented by Formula (1), a suitable interaction occurs between the lubricating layer and the protective layer. Therefore, the fluorine-containing ether compound represented by Formula (1) can form a lubricating layer having excellent chemical substance resistance and a strong pickup minimizing effect.

$R^4$ is a divalent linking group represented by Formula (3-1) or (3-2). The both terminals of $R^4$ are oxygen atoms. The both terminals of $R^4$ are bonded to a methylene group that is bonded to $R^3$ via an ether bond.

$R^4$ has a main chain moiety that forms the chain structure of the fluorine-containing ether compound and a side chain moiety branching from the main chain moiety at carbon atoms bonded to oxygen atoms arranged at both terminals of $R^4$ via 1 to 3 methylene groups and linked by an ether bond. The side chain moiety has a primary hydroxy group arranged at the tip and has a linking group containing a methylene group ($—CH_2—$) that bonds a carbon atom to which a primary hydroxy group is bonded and an oxygen atom (etheric oxygen atom) that is bonded to a carbon atom in the main chain moiety.

$—(CH_2)_{n3}OH$ in Formula (3-1) or $—CH_2CH_2OCH_2CH_2OH$ in Formula (3-2) is bonded to two oxygen atoms arranged at both terminals of $R^4$ and the carbon atom bonded via 1 to 3 methylene groups, as a side chain moiety, via an ether bond. In the present embodiment, when the side chain moiety for $R^4$ is ether-bonded to the carbon atom that forms the main chain moiety for $R^4$, the side chain moiety for $R^4$ has better flexibility, compared to when the side chain moiety for $R^4$ is directly bonded (bonded via a carbon-carbon bond) to the carbon atom that forms the main chain moiety for $R^4$. Furthermore, in the present embodiment, the side chain moiety for $R^4$ has a chain structure containing a linking group and having an appropriate length. Therefore, the side chain moiety for $R^4$ easily interacts with the active sites on the protective layer.

In Formula (3-1), n3 is an integer of 2 to 4. When n3 is 2 or more, the distance between the primary hydroxy group contained in $R^4$ and a bulky portion such as the PFPE chain in the fluorine-containing ether compound or tertiary carbon that is a carbon atom which forms the main chain moiety for $R^4$ and to which the side chain moiety for $R^4$ is ether-bonded becomes sufficiently long, and the primary hydroxy group contained in $R^4$ can easily freely move. In addition, when n3 is 4 or less, the flexibility of $—(CH_2)_{n3}OH$ in Formula (3-1) is maintained. n3 is preferably 2 to 3 and most preferably 2 because $—(CH_2)_{n3}OH$ can flexibly move.

In Formula (3-1), y1 is an integer of 1 to 3, and y2 is an integer of 1 to 3. At least one of y1 and y2 is 1. Since at least one of y1 and y2 is 1, a fluorine-containing ether compound that is easy to produce is obtained. Since y2 when only y1 between y1 and y2 is 1 (or y1 when only y2 is 1) maintains the flexibility of the entire divalent linking group represented by Formula (3-1), it is 3 or less and preferably 2 or less. Since y1 and y2 maintain the flexibility of the entire divalent linking group represented by Formula (3-1), more preferably, y1 is 1 and y2 is 1.

In Formula (3-2), $—CH_2CH_2OCH_2CH_2OH$ contains an ether bond (—O—). Therefore, $—CH_2CH_2OCH_2CH_2OH$ in Formula (3-2) maintains flexibility of movement.

In Formula (3-2), y3 is an integer of 1 to 3, and y4 is an integer of 1 to 3. At least one of y3 and y4 is 1. Since at least one of y3 and y4 is 1, a fluorine-containing ether compound that is easy to produce is obtained. Since y4 when only y3 between y3 and y4 is 1 (or y3 when only y4 is 1) maintains the flexibility of the entire divalent linking group represented by Formula (3-2), it is 3 or less and preferably 2 or less. Since y3 and y4 maintain the flexibility of the entire divalent linking group represented by Formula (3-2), more preferably, y3 is 1 and y4 is 1.

In Formula (1), when x is 2, two $R^4$'s may be the same as or different from each other. When two $R^4$'s are the same, this is preferable because a fluorine-containing ether compound that is easy to produce is obtained. "Two $R^4$'s are the same" means that atoms contained in two $R^4$'s are arranged symmetrically with respect to $R^3$ arranged in the center of the chain structure of the molecule. That is, when x is 2, the fluorine-containing ether compound represented by Formula (1) is preferably a fluorine-containing ether compound in which two $R^4$'s are Formula (3-1), n3's in Formula (3-1) for two $R^4$'s are the same, and y1 and y2 in Formula (3-1) for two $R^4$'s are values that are symmetrical with respect to $R^3$ arranged in the center of the chain structure or a fluorine-containing ether compound in which two $R^4$'s are Formula (3-2), and y3 and y4 in Formula (3-2) for two $R^4$'s are values that are symmetrical with respect to $R^3$ arranged in the center of the chain structure. For example, when $R^4$ on the side of $R^1$ is represented by Formula (3-1), in Formula (3-1), y1 is 1 and y2 is 2, $R^4$ on the side of $R^6$ is represented by Formula (3-1), in Formula (3-1), y1 is 2 and y2 is 1, and the values of n3 in Formula (3-1) are all the same, two $R^4$'s are the same. In addition, for example, when $R^4$ on the side of $R^1$ is represented by Formula (3-2), in Formula (3-2), y3 is 1 and y4 is 2, $R^4$ on the side of $R^6$ is represented by Formula (3-2), and in Formula (3-2), y3 is 2 and y4 is 1, two $R^4$'s are the same.

In the fluorine-containing ether compound represented by Formula (1), preferably, $R^2$ is Formula (2-1), $R^5$ is Formula (2-3), and all x $R^4$'s are Formula (3-1). In this case, more preferably, in Formula (3-1), y1 is 1 and y2 is 1. In addition, more preferably, all of the values of n1 in Formula (2-1), n2 in Formula (2-3) and n3 in Formula (3-1) are the same. This is because a fluorine-containing ether compound that can be easily and efficiently produced is obtained.

In the fluorine-containing ether compound represented by Formula (1), preferably, $R^2$ is Formula (2-2), $R^5$ is Formula (2-4), and all x $R^4$'s are Formula (3-2). This is because a fluorine-containing ether compound that can be easily and efficiently produced is obtained. When $R^2$ is Formula (2-2), $R^5$ is Formula (2-4), and all x $R^4$'s are Formula (3-2), more preferably, in Formula (3-2), y3 is 1 and y4 is 1.

(PFPE Chain Represented by $R^3$)

In the fluorine-containing ether compound represented by Formula (1), (x+1) $R^3$'s are each independently a perfluoropolyether chain. When the lubricant containing the fluorine-containing ether compound of the present embodiment is applied onto the protective layer to form a lubricating layer, the PFPE chain represented by $R^3$ covers the surface of the protective layer, imparts lubricity to the lubricating layer, and reduces the frictional force between the magnetic head and the protective layer. The PFPE chain represented by $R^3$ is appropriately selected depending on the performance required for the lubricant containing the fluorine-containing ether compound and the like.

In the fluorine-containing ether compound represented by Formula (1), when x is 1 or 2, some or all of two or three $R^3$'s may be the same as or different from each other. All of the (x+1) $R^3$'s are preferably the same. This is because the coating of the fluorine-containing ether compound on the protective layer becomes uniform, and a lubricating layer having better adhesion is formed. "Two or more $R^3$'s among (x+1) $R^3$'s are the same" means that, among (x+1) $R^3$'s, two or more $R^3$'s have the same repeating unit structure of the PFPE chain. The same $R^3$ include those having the same repeating unit structure but different average degrees of polymerization.

Examples of PFPE chains represented by $R^3$ include those composed of perfluoroalkylene oxide polymers or copolymers. Examples of perfluoroalkylene oxides include perfluoromethylene oxides, perfluoroethylene oxides, perfluoro-n-propylene oxides, perfluoroisopropylene oxides, and perfluorobutylene oxides.

(x+1) $R^3$'s in Formula (1) are each independently preferably a PFPE chain represented by the following Formula (4) derived from a perfluoroalkylene oxide polymer or copolymer.

$$-(CF_2)_{w1}-O-(CF_2CF_2CF_2O)_{w2}-(CF_2CF_2O)_{w3}-(CF_2CF_2CF_2O)_{w4}-(CF_2CF_2CF_2CF_2O)_{w5}-(CF_2)_{w6}- \quad (4)$$

(in Formula (4), w2, w3, w4, and w5 indicate an average degree of polymerization and each independently represent 0 to 20; provided that all of w2, w3, w4, and w5 are not 0 at the same time; w1 and w6 are an average value representing the number of $CF_2$'s and each independently represent 1 to 3; and the arrangement order of repeating units ($CF_2O$), ($CF_2CF_2O$), ($CF_2CF_2CF_2O$), and ($CF_2CF_2CF_2CF_2O$) in Formula (4) is not particularly limited).

In Formula (4), w2, w3, w4, and w5 indicate an average degree of polymerization and each independently represent 0 to 20, and are preferably 0 to 15 and more preferably 0 to 10. They may be 1 to 8, 2 to 6, 3 to 5 or the like.

In Formula (4), w1 and w6 are an average value indicating the number of $CF_2$'s, and each independently represent 1 to 3. w1 and w6 are determined according to the structure of repeating units arranged at the ends of the chain structure in the PFPE chain represented by Formula (4).

In Formula (4), ($CF_2O$), ($CF_2CF_2O$), ($CF_2CF_2CF_2O$), and ($CF_2CF_2CF_2CF_2O$) are repeating units. The arrangement order of repeating units in Formula (4) is not particularly limited. In addition, the number of types of repeating units in Formula (4) is not particularly limited.

(x+1) $R^3$'s in Formula (1) are each independently preferably any one selected from among PFPE chains represented by the following Formulae (4-1) to (4-4).

When (x+1) $R^3$'s are each independently any one selected from among PFPE chains represented by Formulae (4-1) to (4-4), a fluorine-containing ether compound which can form a lubricating layer having favorable lubricity is obtained. In addition, when (x+1) $R^3$'s are each independently any one selected from among PFPE chains represented by Formulae (4-1) to (4-4), the ratio of the number of oxygen atoms (the number of ether bonds (—O—)) to the number of carbon atoms in the PFPE chain is appropriate. Therefore, the fluorine-containing ether compound having an appropriate hardness is obtained. Therefore, the fluorine-containing ether compound applied onto the protective layer is unlikely to aggregate on the protective layer, and a thinner lubricating layer can be formed at a sufficient coating rate. In addition, since the fluorine-containing ether compound has appropriate flexibility, a lubricating layer having better chemical substance resistance can be formed.

$$-CF_2-(OCF_2CF_2)_h-(OCF_2)_i-OCF_2- \quad (4\text{-}1)$$

(in Formula (4-1), h and i indicate an average degree of polymerization, h represents 1 to 20, and i represents 0 to 20).

$$-CF_2CF_2-(OCF_2CF_2CF_2)_j-OCF_2CF_2- \quad (4\text{-}2)$$

(in Formula (4-2), j indicates an average degree of polymerization and represents 1 to 15).

$$-CF_2CF_2CF_2-(OCF_2CF_2CF_2CF_2)_k-OCF_2CF_2CF_2- \quad (4\text{-}3)$$

(in Formula (4-3), k indicates an average degree of polymerization and represents 1 to 10).

$$-(CF_2)_{w7}-O-(CF_2CF_2CF_2O)_{w8}-(CF_2CF_2O)_{w9}-(CF_2)_{w10}- \quad (4\text{-}4)$$

(in Formula (4-4), w8 and w9 indicate an average degree of polymerization and each independently represent 1 to 20; w7 and w10 are an average value representing the number of $CF_2$'s and each independently represent 1 to 2).

In Formula (4-1), the arrangement order of repeating units ($OCF_2CF_2$) and ($OCF_2$) is not particularly limited. In Formula (4-1), the number h of ($OCF_2CF_2$)'s and the number i of ($OCF_2$)'s may be the same as or different from each other. The PFPE chain represented by Formula (4-1) may be a polymer of ($OCF_2CF_2$). In addition, the PFPE chain represented by Formula (4-1) may be any of a random copolymer, a block copolymer, and an alternating copolymer composed of ($OCF_2CF_2$) and ($OCF_2$).

In Formulae (4-1) to (4-3), since h indicating an average degree of polymerization is 1 to 20, i is 0 to 20, j is 1 to 15, and k is 1 to 10, a fluorine-containing ether compound which can form a lubricating layer having favorable lubricity is obtained. In addition, in Formulae (4-1) to (4-3), when h and i indicating an average degree of polymerization are 20 or less, j is 15 or less, and k is 10 or less, this is preferable because the viscosity of the fluorine-containing ether compound does not become too high, and a lubricant containing this is easily applied. h, i, j, and k indicating an average degree of polymerization are preferably 1 to 10, more preferably 1.5 to 8, and still more preferably 2 to 7 because a fluorine-containing ether compound which easily wets and spreads on the protective layer and allows a lubricating layer having a uniform film thickness to be obtained is obtained.

In Formula (4-4), the arrangement order of repeating units ($CF_2CF_2CF_2O$) and ($CF_2CF_2O$) is not particularly limited. In Formula (4-4), the number w8 of ($CF_2CF_2CF_2O$)'s and the number w9 of ($CF_2CF_2O$)'s, which indicate an average degree of polymerization, may be the same as or different from each other. Formula (4-4) may contain any of a random copolymer, a block copolymer, and an alternating copolymer composed of monomer units ($CF_2CF_2CF_2O$) and ($CF_2CF_2O$).

In Formula (4-4), w8 and w9 indicating an average degree of polymerization are each independently 1 to 20, preferably 1 to 15, and more preferably 1 to 10.

In Formula (4-4), w7 and w10 are an average value indicating the number of $CF_2$'s and each independently represent 1 to 2. w7 and w10 are determined according to the structure of repeating units arranged at the ends of the chain structure in the PFPE chain represented by Formula (4-4).

(Terminal Groups Represented by $R^1$ and $R^6$)

In the fluorine-containing ether compound represented by Formula (1), terminal groups represented by $R^1$ and $R^6$ are each independently an organic group having 1 to 50 carbon atoms. The terminal groups represented by $R^1$ and $R^6$ are each independently preferably an organic group having 1 to 20 carbon atoms and more preferably an organic group having 2 to 10 carbon atoms.

The terminal group represented by $R^1$ preferably has a carbon atom at the end that is bonded to $R^2$. The terminal group represented by $R^6$ preferably has a carbon atom at the end that is bonded to $R^5$. Accordingly, when the terminal group represented by $R^1$ (or $R^6$) has a polar group, the distance between the primary hydroxy group of $R^2$ (or $R^5$) and the polar group of $R^1$ (or) $R^6$ becomes even more appropriate. As a result, the primary hydroxy group of $R^2$ (or $R^5$) adjacent to $R^1$ (or $R^6$) is much less likely to be inhibited from bonding to the active sites on the protective layer due to the polar group of $R^1$ (or $R^6$).

The terminal groups represented by $R^1$ and $R^6$ preferably do not contain a secondary hydroxy group (that is, the fluorine-containing ether compound represented by Formula (1) does not contain a secondary hydroxy group) in order to further improve chemical substance resistance.

$R^1$ and $R^6$ are each independently preferably any of an organic group having a polar group, an organic group having a carbon-carbon unsaturated bond, and an organic group having both a polar group and a carbon-carbon unsaturated bond.

When the terminal group has a polar group, the polar group is preferably at least one selected from the group consisting of a hydroxy group (—OH), an amino group (—$NR^7R^8$; $R^7$ and $R^8$ are each independently a hydrogen atom or an organic group), a carboxy group (—COOH), a formyl group (—(C═O)H), a carbonyl group (—CO—), a sulfo group (—$SO_3H$), a cyano group (—CN), and a group having an amide bond (—$NR^9COR^{10}$ or —$CONR^{11}R^{12}$; $R^9$, $R^{10}$, $R^{11}$ and $R^{12}$ are each independently a hydrogen atom or an organic group). Here, as shown in the above formula, the "group having an amide bond" includes both a group that is bonded to an organic group at a carbon atom constituting an amide bond (for example, a carboxamide group (—C(═O)$NH_2$)) and a group that is bonded to an organic group at a nitrogen atom constituting an amide bond (for example, acetamide group (—NHC(═O) $CH_3$)). In the group having an amide bond, $R^9$ and $R^{10}$ may be bonded to each other to form a ring, and $R^{11}$ and $R^{12}$ may be bonded to each other to form a ring. $R^9$, $R^{10}$, $R^{11}$ and $R^{12}$ in the group having an amide bond are each independently preferably selected from the group consisting of a hydrogen atom, a methyl group, an ethyl group, a propyl group, and a butyl group.

Among these polar groups, at least one polar group selected from the group consisting of a hydroxy group, a cyano group, and a group having an amide bond is more preferable. This is because a fluorine-containing ether compound which can form a lubricating layer having better chemical substance resistance and a stronger pickup minimizing effect is obtained.

When the terminal group has polar groups, the number of polar groups is preferably 1 to 3 and more preferably 1 to 2. When the number of polar groups is 2 or more, some or all of the polar groups may be the same as or different from each other.

The organic group having a polar group is preferably represented by $-CH_2-Y$, $-CH_2CH_2-Y$, $-CH_2-O-CH_2CH_2-Y$, $-CH_2-O-CH_2CH_2CH_2-Y$, $-CH_2-O-CH_2CH(OH)CH_2-O-CH_2CH_2-Y$, or $-CH_2-O-CH_2CH(OH)CH_2-O-CH_2CH_2CH_2-Y$ (in the formulae, Y is a polar group).

When the terminal group has a carbon-carbon unsaturated bond, the terminal group is preferably an organic group having at least one carbon-carbon unsaturated bond selected from the group consisting of an optionally substituted aromatic hydrocarbon group, an unsaturated heterocyclic group, an alkenyl group, and an alkynyl group.

Specific examples of optionally substituted aromatic hydrocarbon groups include a phenyl group, methoxyphenyl group, fluorinated phenyl group, naphthyl group, and methoxynaphthyl group.

Examples of unsaturated heterocyclic groups include a pyrrolyl group, pyrazolyl group, imidazolyl group, furyl group, furfuryl group, oxazolyl group, isooxazolyl group, thienyl group, thiazolyl group, isothiazolyl group, pyridyl group, pyrimidinyl group, pyridazinyl group, pyrazinyl group, indolinyl group, benzofuranyl group, benzothienyl group, benzoimidazolyl group, benzooxazolyl group, benzothiazolyl group, benzopyrazolyl group, benzoisooxazolyl group, benzoisothiazolyl group, quinolyl group, isoquinolyl group, quinazolinyl group, quinoxalinyl group, phthalazinyl group, and cinnolinyl group.

Examples of alkenyl groups include an allyl group and butenyl group.

Examples of alkynyl groups include a propargyl group.

When the terminal group has a carbon-carbon unsaturated bond, the terminal group is preferably an organic group having one carbon-carbon unsaturated bond selected from the group consisting of a phenyl group, a methoxyphenyl group, a naphthyl group, a thienyl group, and an allyl group. This is because a fluorine-containing ether compound which can form a lubricating layer having better chemical substance resistance and a stronger pickup minimizing effect is obtained.

The organic group having a carbon-carbon unsaturated bond is preferably one represented by $-CH_2-O-Z$ or $-CH_2CH_2-O-Z$ (in the formula, Z is any one selected from the group consisting of an optionally substituted aromatic hydrocarbon group, an unsaturated heterocyclic group, an alkenyl group, and an alkynyl group).

The organic group having both a polar group and a carbon-carbon unsaturated bond is preferably one represented by $-CH_2-O-CH_2CH(OH)CH_2-O-Z$, or $-CH_2CH_2-O-CH_2CH(OH)CH_2-O-Z$ (in the formula, Z is any one selected from the group consisting of an optionally substituted aromatic hydrocarbon group, an unsaturated heterocyclic group, an alkenyl group, and an alkynyl group).

In the fluorine-containing ether compound represented by Formula (1), $R^1$ and $R^6$ are each independently preferably a terminal group represented by any of the following Formulae (5-1) to (5-8). The following Formulae (5-1) to (5-3) are all organic groups having only one primary hydroxy group, which is a polar group. The following Formula (5-4) is an organic group having one primary hydroxy group and one secondary hydroxy group as polar groups. The following Formula (5-5) is an organic group having one secondary hydroxy group as a polar group and also having one allyl group which is a group having a carbon-carbon unsaturated bond. The following Formula (5-6) is an organic group having one secondary hydroxy group as a polar group and also having one phenyl group which is a group having a carbon-carbon unsaturated bond. The following Formula (5-7) is an organic group having one cyano group which is a polar group. The following Formula (5-8) is an organic group having one group having an amide bond ($-NHCOCH_3$), which is a polar group.

[Chem. 5]

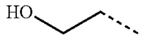
(5-1)

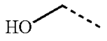
(5-2)

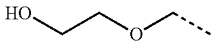
(5-3)

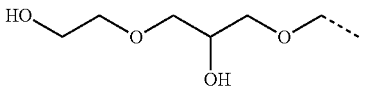
(5-4)

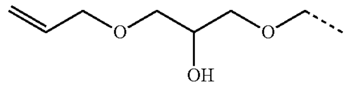
(5-5)

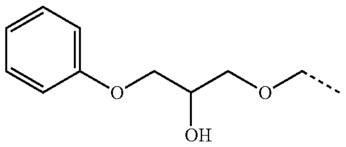
(5-6)

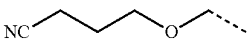
(5-7)

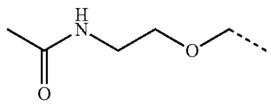
(5-8)

(in Formulae (5-1) to (5-8), a dotted line indicates a bond that is bonded to a carbon atom of $R^2$ or $R^5$).

When the terminal group represented by $R^1$ and/or $R^6$ has a polar group, the lubricating layer containing the fluorine-containing ether compound is preferable because it has better adhesion to the protective layer and can be made thinner. The reason for this will be described below.

In the side chain moieties of $R^2$ and $R^5$, a carbon atom to which a primary hydroxy group arranged at the tip is bonded and an oxygen atom that is bonded to a carbon atom in the main chain moiety are bonded by a linking group containing a methylene group ($-CH_2-$). Therefore, even if $R^1$ (or $R^6$) contains a polar group, the distance between the polar group of $R^1$ (or $R^6$) and the primary hydroxy group of $R^2$ (or $R^5$) is appropriate. As a result, the primary hydroxy group of $R^2$ (or $R^5$) and the polar group of $R^1$ (or $R^6$) are less likely to be inhibited from bonding to the active sites on the protective layer due to other polar groups, and the primary hydroxy group of $R^2$ (or $R^5$) and the polar group of $R^1$ (or $R^6$) are unlikely to aggregate Therefore, the primary hydroxy group of $R^2$ (or $R^5$) and the polar group of $R^1$ (or $R^6$) can each be independently adsorbed to the active sites on the protective layer. As a result, a lubricating layer containing the fluorine-containing ether compound in which the terminal group represented by $R^1$ and/or $R^6$ has a polar group has better adhesion to the protective layer, and exhibits favorable chemical substance resistance even if the thickness is thin, and has a strong pickup minimizing effect.

In the fluorine-containing ether compound represented by Formula (1), a total number of polar groups contained in $R^1$ and $R^6$ is preferably 1 or more and more preferably 2 or more in order to improve the adhesion to the protective layer and realize a thinner lubricating layer. In the fluorine-containing ether compound represented by Formula (1), the total number of polar groups contained in $R^1$ and $R^6$ is preferably 4 or less, more preferably 3 or less, and most preferably 2 or less in order to prevent the number of polar groups from becoming too large and polar groups that do not participate in bonding with the protective layer from being generated.

In addition, when the terminal group represented by $R^1$ and/or $R^6$ has a carbon-carbon unsaturated bond, this is preferable because a lubricating layer containing the fluorine-containing ether compound has better adhesion to the protective layer and can be made thinner. The reason for this will be described below.

Among a plurality of functional groups (active sites) present on the protective layer, there are locally charged sites and sites with a wide charge distribution. The hydroxy groups contained in $R^2$, $R^4$ and $R^5$ in Formula (1) and the carbon-carbon unsaturated bond contained in the terminal group represented by $R^1$ and/or $R^6$ are adsorbed to different sites on the protective layer. Specifically, the hydroxy groups contained in $R^2$, $R^4$ and $R^5$ in Formula (1) exhibit an adsorption ability when hydrogen atoms interact with locally charged sites on the protective layer via a hydrogen bond. On the other hand, since the carbon-carbon unsaturated bond contained in the terminal group represented by $R^1$ and/or $R^6$ has a non-local charge, it interacts with sites with a wide charge distribution on the protective layer and thus exhibits an adsorption ability.

Therefore, in Formula (1), the hydroxy groups contained in $R^2$, $R^4$ and $R^5$ and the carbon-carbon unsaturated bond contained in the terminal group represented by $R^1$ and/or $R^6$ can each independently interact with functional groups (active sites) on the protective layer. As a result, a lubricating layer containing the fluorine-containing ether compound in which the terminal group represented by $R^1$ and/or $R^6$ has a carbon-carbon unsaturated bond has better adhesion to the protective layer and exhibits better chemical substance resistance even if the thickness is thin, and has a strong pickup minimizing effect.

In the fluorine-containing ether compound represented by Formula (1), the types of terminal groups represented by $R^1$ and $R^6$ can be appropriately selected depending on the performance required for the lubricant containing the fluorine-containing ether compound and the like.

In the fluorine-containing ether compound represented by Formula (1), $R^1$ and $R^6$ may be the same as or different from each other. When $R^1$ and $R^6$ are the same, the coating of the fluorine-containing ether compound on the protective layer becomes more uniform, and a lubricating layer having better adhesion can be formed.

In the fluorine-containing ether compound represented by Formula (1), $R^1$—$R^2$— and $R^6$—$R^5$— in Formula (1) are preferably the same. This is because a fluorine-containing ether compound that can be easily and efficiently produced is obtained. In the fluorine-containing ether compound represented by Formula (1), more preferably, all (x+1) $R^3$'s in Formula (1) are the same, all x $R^4$ are the same, and $R^1$—$R^2$— and $R^6$—$R^5$— are the same. This is because a fluorine-containing ether compound that can be more easily and efficiently produced is obtained.

Specifically, the fluorine-containing ether compound represented by Formula (1) is preferably a compound represented by any of the following Formulae (A) to (X), and (XX).

When the compound represented by Formula (1) is a compound represented by any of the following Formulae (A) to (X), and (XX), raw materials are easily available, and moreover, it is possible to form a lubricating layer having favorable chemical substance resistance and a strong pickup minimizing effect.

In the compounds represented by the following Formulae (A) to (X), and (XX), $Rf_1$, $Rf_2$, and $Rf_3$ representing PFPE chains have the following structures. That is, in the compounds represented by the following Formulae (A) to (K), (N) to (R), (T) to (W), and (XX), $Rf_1$ is the PFPE chain represented by Formula (4-1). In the compounds represented by the following Formulae (L), (S), and (X), $Rf_2$ is the PFPE chain represented by Formula (4-2). In the compound represented by the following Formula (M), $Rf_3$ is the PFPE chain represented by Formula (4-3). Here, in Formulae (A) to (X), and (XX), since h and i in $Rf_1$, j in $Rf_2$ and k in $Rf_3$, which represent the PFPE chain, are values indicating an average degree of polymerization, they are not necessarily an integer.

[Chem. 6]

$Rf_1$ = 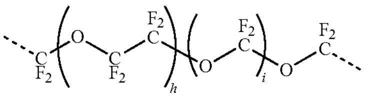

$Rf_2$ = 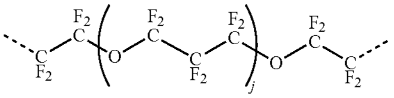

$Rf_3$ = 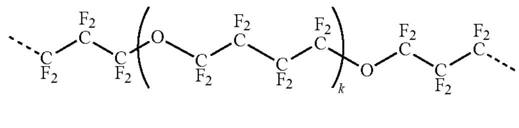

In all of the compounds represented by the following Formulae (A) to (X), and (XX), $R^2$ is the linking group represented by Formula (2-1) or (2-2), and $R^5$ is the linking group represented by Formula (2-3) or (2-4).

In all of the compounds represented by the following Formulae (A) to (M), in Formula (1), x is 0, and the structure does not contain $R^4$. In all of the compounds represented by the following Formulae (N) to (X), and (XX), in Formula (1), x is 1 or 2, and the structure contains one or two $R^4$'s. In all of the compounds represented by the following Formulae (N) to (X), and (XX), $R^4$ is the linking group represented by Formula (3-1) or (3-2).

In the compounds represented by the following Formulae (A) to (H), in Formula (1), x is 0. $R^1$ and $R^6$ are a terminal group represented by any of Formulae (5-1) to (5-8). All $R^2$'s are the linking group represented by Formula (2-1), and n1 is 2. All $R^5$'s are the linking group represented by Formula (2-3), and n2 is 2. All $R^3$'s are the PFPE chain represented by Formula (4-1).

In the compounds represented by the following Formulae (I) and (J), in Formula (1), x is 0. In all of the compounds represented by the following Formulae (I) and (J), $R^1$ and $R^6$ are the terminal group represented by Formula (5-1), and $R^3$ is the PFPE chain represented by Formula (4-1).

In the compound represented by the following Formula (I), $R^2$ is the linking group represented by Formula (2-1), and n1 is 3. $R^5$ is the linking group represented by Formula (2-3), and n2 is 3.

In the compound represented by the following Formula (J), $R^2$ is the linking group represented by Formula (2-1), and n1 is 4. $R^5$ is the linking group represented by Formula (2-3), and n2 is 4.

In the compound represented by the following Formula (K), in Formula (1), x is 0. $R^1$ and $R^6$ are the terminal group represented by Formula (5-1). $R^2$ is the linking group represented by Formula (2-2). $R^5$ is the linking group represented by Formula (2-4). $R^3$ is the PFPE chain represented by Formula (4-1).

In the compounds represented by the following Formulae (L) and (M), in Formula (1), x is 0. In all of the compounds represented by the following Formulae (L) and (M), $R^1$ and $R^6$ are the terminal group represented by Formula (5-1). All $R^2$'s are the linking group represented by Formula (2-1) and n1 is 2. All $R^5$'s are the linking group represented by Formula (2-3) and n2 is 2.

In the compound represented by the following Formula (L), $R^3$ is the PFPE chain represented by Formula (4-2). In the compound represented by the following Formula (M), $R^3$ is the PFPE chain represented by Formula (4-3).

In all of the compounds represented by the following Formulae (N) to (P), in Formula (1), x is 1. $R^2$ is the linking group represented by Formula (2-1), and n1 is 2. $R^5$ is the linking group represented by Formula (2-3), and n2 is 2. $R^4$ is the linking group represented by Formula (3-1), n3 is 2, y1 is 1, and y2 is 1. In the compounds represented by the following Formulae (N) to (P), both two $R^3$'s are the PFPE chain represented by Formula (4-1).

In the compound represented by the following Formula (N), $R^1$ and $R^6$ are the terminal group represented by Formula (5-1). In the compound represented by the following Formula (O), $R^1$ and $R^6$ are the terminal group represented by Formula (5-3). In the compound represented by the following Formula (P), $R^1$ and $R^6$ are the terminal group represented by Formula (5-7).

In the compound represented by the following Formula (Q), in Formula (1), x is 1. $R^1$ and $R^6$ are the terminal group represented by Formula (5-1). $R^2$ is the linking group represented by Formula (2-1), and n1 is 3. $R^5$ is the linking group represented by Formula (2-3), and n2 is 3. $R^4$ is the linking group represented by Formula (3-1), n3 is 3, y1 is 1, and y2 is 1. Both two $R^3$'s are the PFPE chain represented by Formula (4-1).

In the compound represented by the following Formula (R), in Formula (1), x is 1. $R^1$ and $R^6$ are the terminal group represented by Formula (5-1). $R^2$ is the linking group represented by Formula (2-2). $R^5$ is the linking group represented by Formula (2-4). $R^4$ is the linking group represented by Formula (3-2), y3 is 1, and y4 is 1. Both two $R^3$'s are the PFPE chain represented by Formula (4-1).

In the compound represented by the following Formula(S), in Formula (1), x is 1. $R^1$ and $R^6$ are the terminal group represented by Formula (5-1). $R^2$ is the linking group represented by Formula (2-1), and n1 is 2. $R^5$ is the linking group represented by Formula (2-3), and n2 is 2. $R^4$ is the linking group represented by Formula (3-1), n3 is 2, y1 is 1, and y2 is 1. Both two $R^3$'s are the PFPE chain represented by Formula (4-2).

In all of the compounds represented by the following Formulae (T) to (V), in Formula (1), x is 2. $R^2$ is the linking group represented by Formula (2-1), and n1 is 2. $R^5$ is the linking group represented by Formula (2-3), and n2 is 2. Both two $R^4$'s are the linking group represented by Formula (3-1), n3 is 2, y1 is 1, and y2 is 1. All three $R^3$'s are the PFPE chain represented by Formula (4-1).

In the compound represented by the following Formula (T), $R^1$ and $R^6$ are the terminal group represented by Formula (5-1). In the compound represented by the following Formula (U), $R^1$ and $R^6$ are the terminal group represented by Formula (5-3). In the compound represented by the following Formula (V), $R^1$ and $R^6$ are the terminal group represented by Formula (5-7).

In the compound represented by the following Formula (W), in Formula (1), x is 2. $R^1$ and $R^6$ are the terminal group represented by Formula (5-1). $R^2$ is the linking group represented by Formula (2-2). $R^5$ is the linking group represented by Formula (2-4). Both two $R^4$'s are the linking group represented by Formula (3-2), y3 is 1, and y4 is 1. All three $R^3$'s are the PFPE chain represented by Formula (4-1).

In the compound represented by the following Formula (X), in Formula (1), x is 2. $R^1$ and $R^6$ are the terminal group represented by Formula (5-1). $R^2$ is the linking group represented by Formula (2-1), and n1 is 2. $R^5$ is the linking group represented by Formula (2-3), and n2 is 2. Both two $R^4$'s are the linking group represented by Formula (3-1), n3 is 2, y1 is 1, and y2 is 1. All three $R^3$'s are the PFPE chain represented by Formula (4-2).

In the compound represented by the following Formula (XX), in Formula (1), x is 1. $R^1$ and $R^6$ are the terminal group represented by Formula (5-2). $R^2$ is the linking group represented by Formula (2-1), and n1 is 2. $R^5$ is the linking group represented by Formula (2-3), and n2 is 2. $R^4$ is the linking group represented by Formula (3-1), n3 is 2, y1 is 1, and y2 is 1. Both two $R^3$'s are the PFPE chain represented by Formula (4-1).

[Chem. 7]

(A)

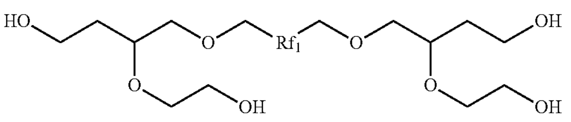

(B)

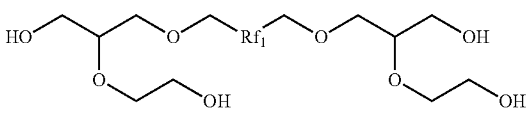

(C)

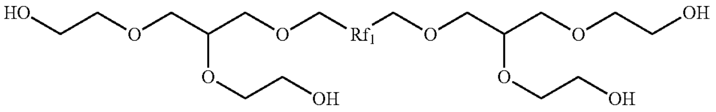

-continued (D)

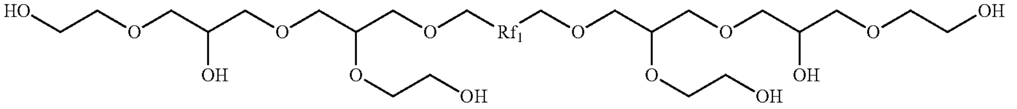

(E)

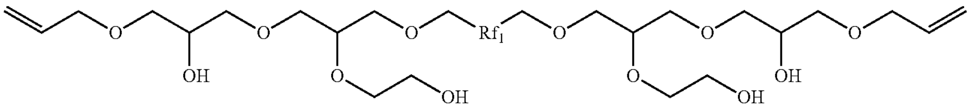

(F)

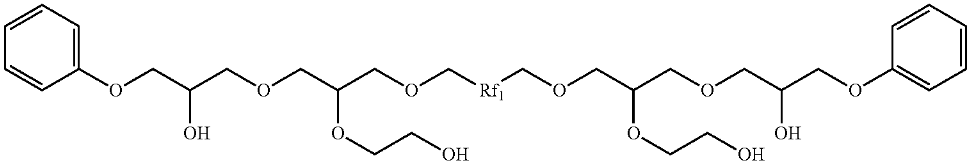

(in Formula (A), in $Rf_1$, h and i indicate an average degree of polymerization, h represents 1 to 20, and i represents 0 to 20).

(in Formula (B), in $Rf_1$, h and i indicate an average degree of polymerization, h represents 1 to 20, and i represents 0 to 20).

(in Formula (C), in $Rf_1$, h and i indicate an average degree of polymerization, h represents 1 to 20, and i represents 0 to 20).

(in Formula (D), in $Rf_1$, h and i indicate an average degree of polymerization, h represents 1 to 20, and i represents 0 to 20).

(in Formula (E), in $Rf_1$, h and i indicate an average degree of polymerization, h represents 1 to 20, and i represents 0 to 20).

(in Formula (F), in $Rf_1$, h and i indicate an average degree of polymerization, h represents 1 to 20, and i represents 0 to 20).

[Chem. 8]

(G)

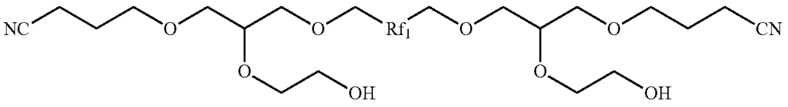

(H)

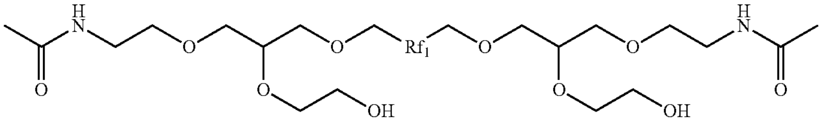

(I)

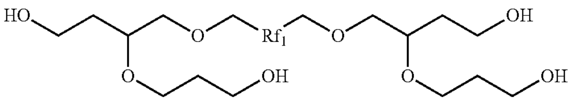

(J)

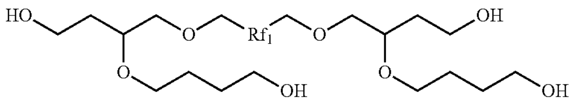

(K)

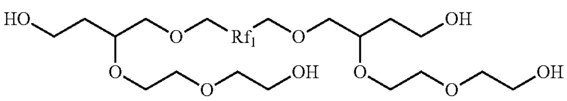

(L)

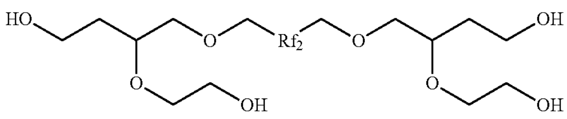

(M)

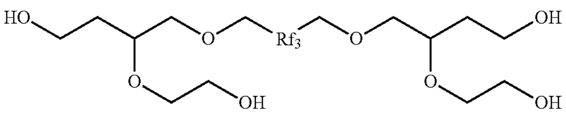

(in Formula (G), in $Rf_1$, h and i indicate an average degree of polymerization, h represents 1 to 20, and i represents 0 to 20).

(in Formula (H), in $Rf_1$, h and i indicate an average degree of polymerization, h represents 1 to 20, and i represents 0 to 20).

(in Formula (I), in $Rf_1$, h and i indicate an average degree of polymerization, h represents 1 to 20, and i represents 0 to 20).

(in Formula (J), in $Rf_1$, h and i indicate an average degree of polymerization, h represents 1 to 20, and i represents 0 to 20).

(in Formula (K), in $Rf_1$, h and i indicate an average degree of polymerization, h represents 1 to 20, and i represents 0 to 20).

(in Formula (L), in $Rf_2$, j indicates an average degree of polymerization and represents 1 to 15).

(in Formula (M), in $Rf_3$, k indicates an average degree of polymerization and represents 1 to 10).

(in Formula (O), in two $Rf_1$'s, h and i indicate an average degree of polymerization, h represents 1 to 20, and i represents 0 to 20; and in two $Rf_1$'s, average degrees of polymerization may be the same as or different from each other).

(in Formula (P), in two $Rf_1$'s, h and i indicate an average degree of polymerization, h represents 1 to 20, and i represents 0 to 20; and in two $Rf_1$'s, average degrees of polymerization may be the same as or different from each other).

(in Formula (Q), in two Rf's, h and i indicate an average degree of polymerization, h represents 1 to 20, and i represents 0 to 20; and in two $Rf_1$'s, average degrees of polymerization may be the same as or different from each other).

(in Formula (R), in two $Rf_1$'s, h and i indicate an average degree of polymerization, h represents 1 to 20, and i represents 0 to 20; and in two $Rf_1$'s, average degrees of

[Chem. 9]

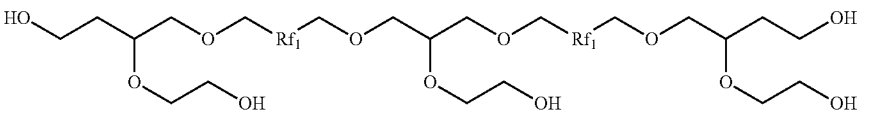
(N)

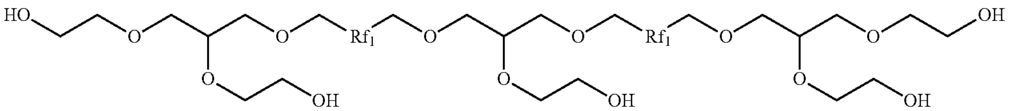
(O)

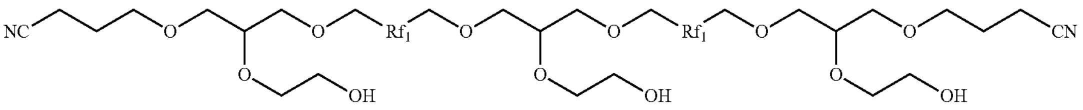
(P)

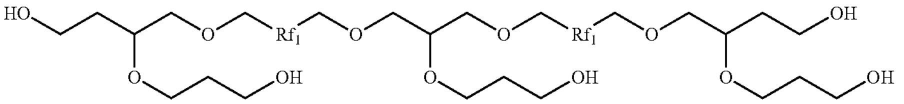
(Q)

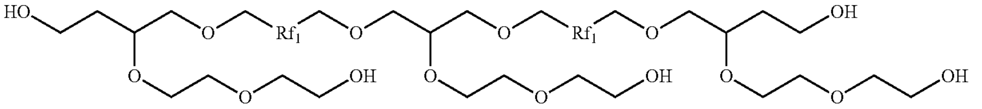
(R)

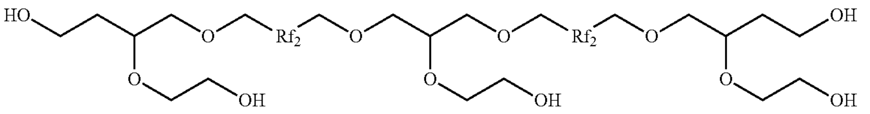
(S)

(in Formula (N), in two $Rf_1$'s, h and i indicate an average degree of polymerization, h represents 1 to 20, and i represents 0 to 20; and in two $Rf_1$'s, average degrees of polymerization may be the same as or different from each other).

polymerization may be the same as or different from each other).

(in Formula(S), in two $Rf_2$'s, j indicates an average degree of polymerization and represents 1 to 15; in two $Rf_2$'s, average degrees of polymerization may be the same as or different from each other).

[Chem. 10]

(T)

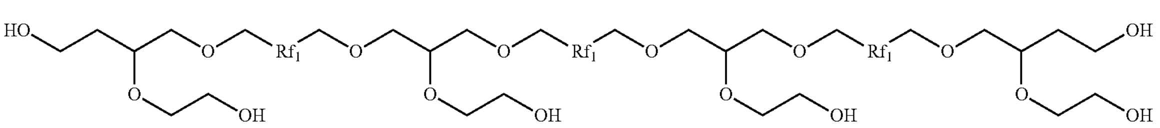

(U)

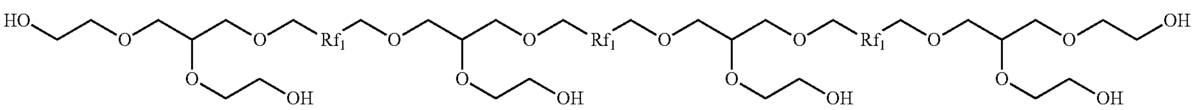

(V)

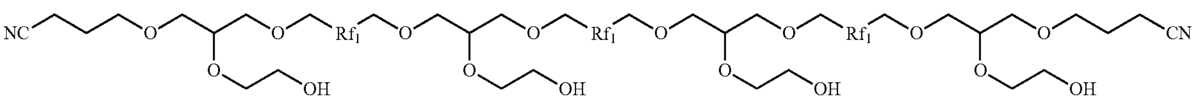

(in Formula (T), in three $Rf_1$'s, h and i indicate an average degree of polymerization, h represents 1 to 20, and i represents 0 to 20; and in three $Rf_1$'s, average degrees of polymerization may be different from each other, and average degrees of polymerization in two or three $Rf_1$'s may be the same).

(in Formula (U), in three $Rf_1$'s, h and i indicate an average degree of polymerization, h represents 1 to 20, and i represents 0 to 20; and in three $Rf_1$'s, average degrees of polymerization may be different from each other, and average degrees of polymerization in two or three $Rf_1$'s may be the same).

(in Formula (V), in three $Rf_1$'s, h and i indicate an average degree of polymerization, h represents 1 to 20, and i represents 0 to 20; and in three $Rf_1$'s, average degrees of polymerization may be different from each other, and average degrees of polymerization in two or three $Rf_1$'s may be the same).

[Chem. 11]

(W)

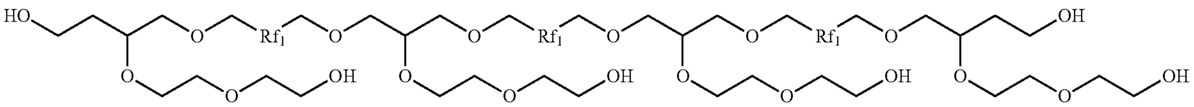

(X)

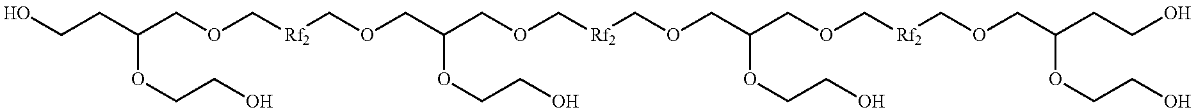

(XX)

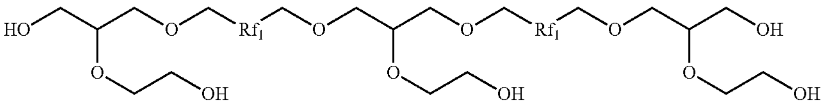

(in Formula (W), in three $Rf_1$'s, h and i indicate an average degree of polymerization, h represents 1 to 20, and i represents 0 to 20; and in three $Rf_1$'s, average degree of polymerization may be different from each other, and average degrees of polymerization in two or three $Rf_1$'s may be the same).

(in Formula (X), in three $Rf_2$'s, j indicates an average degree of polymerization and represents 1 to 15; and in three $Rf_2$'s, average degrees of polymerization may be different from each other, and averages degree of polymerization in two or three $Rf_2$'s may be the same).

(in Formula (XX), in two $Rf_1$'s, h and i indicate an average degree of polymerization, h represents 1 to 20, and i represents 0 to 20; and in two $Rf_1$'s, average degrees of polymerization may be the same as or different from each other).

The number-average molecular weight (Mn) of the fluorine-containing ether compound of the present embodiment is preferably in a range of 500 to 10,000 and particularly preferably in a range of 1,000 to 5,000. When the number-average molecular weight is 500 or more, the lubricating layer composed of the lubricant containing the fluorine-containing ether compound of the present embodiment has excellent heat resistance. The number-average molecular weight of the fluorine-containing ether compound is more preferably 1,000 or more. In addition, when the number-average molecular weight is 10,000 or less, the viscosity of the fluorine-containing ether compound becomes appropriate, and when a lubricant containing this is applied, a lubricating layer having a thin film thickness can be easily formed. The number-average molecular weight of the fluorine-containing ether compound is preferably 5,000 or less because the viscosity becomes one that makes the lubricant easy to handle.

The number-average molecular weight (Mn) of the fluorine-containing ether compound is a value measured through $^1$H-NMR and $^{19}$F-NMR using a AVANCE III 400 (commercially available from Bruker BioSpin). Specifically, the number of repeating units of the PFPE chain is calculated from the integrated value measured by $^{19}$F-NMR to obtain a number-average molecular weight. In the measurement of nuclear magnetic resonance (NMR), a sample is diluted with a hexafluorobenzene/d-acetone (4/1v/v) solvent and used for measurement. The reference for $^{19}$F-NMR chemical shift is-164.7 ppm for the peak of hexafluorobenzene, and the reference for $^1$H-NMR chemical shift is 2.2 ppm for the peak of acetone.

The fluorine-containing ether compound of the present embodiment preferably has a molecular weight dispersity (a ratio of the weight-average molecular weight (Mw)/the number-average molecular weight (Mn)) of 1.3 or less by molecular weight fractionation by an appropriate method.

In the present embodiment, the method for molecular weight fractionation is not particularly limited, and for example, molecular weight fractionation using a silica gel column chromatography method, a gel permeation chromatography (GPC) method or the like, molecular weight fractionation using a supercritical extraction method or the like can be used.

"Production Method"

The method of producing the fluorine-containing ether compound of the present embodiment is not particularly limited, and conventionally known production methods can be used for production. The fluorine-containing ether compound of the present embodiment can be produced, for example, as shown below, using a production method including a first reaction step of forming a main chain moiety that forms a chain structure of a fluorine-containing ether compound and a second reaction step of forming a side chain moiety branching from the main chain moiety.

The first reaction step is preferably a step of synthesizing a first intermediate compound, which is a compound having a structure in which a secondary hydroxy group is arranged in each of main chain moieties for $R^2$ and $R^5$ ($R^2$, $R^4$, and $R^5$ when x is 1 or 2) of the chain structure of the fluorine-containing ether compound in Formula (1).

The second reaction step is preferably a step of chemically modifying the secondary hydroxy group arranged in each of the main chain moieties for $R^2$ and $R^5$ ($R^2$, $R^4$, and $R^5$ when x is 1 or 2) in Formula (1) of the first intermediate compound to form a side chain moiety having a primary hydroxy group.

[First Production Method]

When a fluorine-containing ether compound in which x in Formula (1) is 0 is produced, for example, the following first production method can be used.

First, a fluorine-based compound in which hydroxymethyl groups ($—CH_2OH$) are arranged at both terminals of a perfluoropolyether chain corresponding to $R^3$ in Formula (1) is prepared.

(First Reaction Step)

<When $R^1$ and $R^6$ are the Same>

When a fluorine-containing ether compound in which, in Formula (1), x is 0 and $R^1$ and $R^6$ are the same is produced, in the first reaction step, a hydroxy group of a hydroxymethyl group arranged at both terminals of the fluorine-based compound is reacted with an epoxy compound corresponding to a group in which a group corresponding to $R^1$ and a group corresponding to a main chain moiety for $R^2$ in Formula (1) are bonded (=a group in which a group corresponding to $R^6$ and a group corresponding to a main chain moiety for $R^5$ are bonded).

According to the reaction, a first intermediate compound 1*a* having a group in which a group corresponding to $R^1$ and a group corresponding to a main chain moiety for $R^2$ are bonded (=a group in which a group corresponding to $R^6$ and a group corresponding to a main chain moiety for $R^5$ are bonded) at both terminals of a perfluoropolyether chain corresponding to $R^3$ is obtained. In the first intermediate compound 1*a*, in the group corresponding to a main chain moiety for $R^2$ and the group corresponding to a main chain moiety for $R^5$, one secondary hydroxy group generated by the reaction between the hydroxy group of the hydroxymethyl group and the epoxy group of the epoxy compound in the first reaction step is arranged.

<When $R^1$ and $R^6$ are Different>

When a compound in which, in Formula (1), x is 0 and $R^1$ and $R^6$ are different is produced, in the first reaction step, a hydroxy group of a hydroxymethyl group arranged at one terminal of the fluorine-based compound is reacted with an epoxy compound corresponding to a group in which a group corresponding to $R^1$ and a group corresponding to a main chain moiety for $R^2$ in Formula (1) are bonded. Then, a hydroxy group of a hydroxymethyl group arranged at the other terminal of the fluorine-based compound is reacted with an epoxy compound corresponding to a group in which a group corresponding to $R^6$ and a group corresponding to a main chain moiety for $R^5$ are bonded in Formula (1).

The first reaction step in this case may be a step in which a hydroxy group of a hydroxymethyl group arranged at one terminal of the fluorine-based compound is reacted with an epoxy compound corresponding to a group in which a group corresponding to $R^6$ and a group corresponding to a main chain moiety for $R^5$ are bonded in Formula (1), and a hydroxy group of a hydroxymethyl group arranged at the other terminal of the fluorine-based compound is then reacted with an epoxy compound corresponding to a group in which a group corresponding to $R^1$ and a group corresponding to a main chain moiety for $R^2$ in Formula (1) are bonded.

According to the reaction, a first intermediate compound 1*b* having a group in which a group corresponding to $R^1$ and a group corresponding to a main chain moiety for $R^2$ are bonded at one terminal of a perfluoropolyether chain corresponding to $R^3$ and a group in which a group corresponding to $R^6$ and a group corresponding to a main chain moiety for $R^5$ are bonded at the other terminal is obtained. In the first intermediate compound 1*b*, in the group corresponding to a main chain moiety for $R^2$ and the group corresponding to a main chain moiety for $R^5$, one secondary hydroxy group generated by the reaction between the hydroxy group of the hydroxymethyl group and the epoxy group of the epoxy compound in the first reaction step is arranged.

As the epoxy compound corresponding to the group in which a group corresponding to $R^1$ and a group corresponding to a main chain moiety for $R^2$ in Formula (1) are bonded (or a group in which a group corresponding to $R^6$ and a group corresponding to a main chain moiety for $R^5$ are bonded) used in the first reaction step, for example, compounds represented by the following Formulae (7-1) to (7-8) and the like can be used.

[Chem. 12]

(7-1)

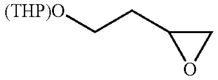

(7-2)

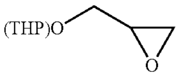

(7-3)

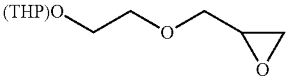

(7-4)

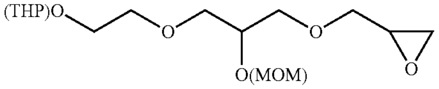

(7-5)

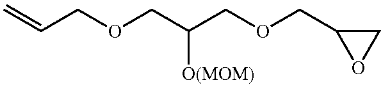

(7-6)

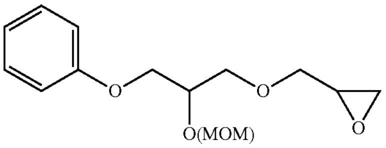

(7-7)

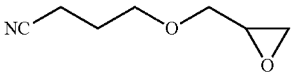

(7-8)

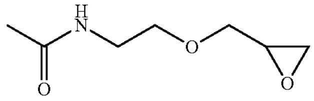

(in Formulae (7-1) to (7-4), THP represents a tetrahydropyranyl group).

(in Formula (7-4) to (7-6), MOM represents a methoxymethyl group).

The epoxy compound used in the first reaction step can be synthesized by, for example, a method of reacting an alcohol having a structure corresponding to $R^1$ (or $R^6$) of a fluorine-containing ether compound to be produced with epichlorohydrin or epibromohydrin. The epoxy compound used in the first reaction step may be synthesized by a method of oxidizing a compound having a carbon-carbon double bond or a commercial product may be purchased and used.

(Second Reaction Step)

<When Side Chain Moiety for $R^2$ and side chain moiety for $R^5$ are the Same>

When a fluorine-containing ether compound in which, in Formula (1), x is 0, and a side chain moiety for $R^2$ and a side chain moiety for $R^5$ are the same is produced, in the second reaction step, one type of halide having a protected hydroxy group corresponding to a side chain moiety for $R^2$ (=a side chain moiety for $R^5$) in Formula (1) is reacted with a secondary hydroxy group of the first intermediate compound 1*a* or first intermediate compound 1*b* generated in the first reaction step to generate a second intermediate compound 2*a*.

<When Side Chain Moiety for $R^2$ and side chain moiety for $R^5$ are Different>

When a fluorine-containing ether compound in which, in Formula (1), x is 0 and a side chain moiety for $R^2$ and a side chain moiety for $R^5$ are different is produced, in the second reaction step, a halide having a protected hydroxy group corresponding to a side chain moiety for $R^2$ in Formula (1), and a halide having a protected hydroxy group corresponding to a side chain moiety for $R^5$ are sequentially reacted with a secondary hydroxy group of the first intermediate compound 1*a* or first intermediate compound 1*b* generated in the first reaction step using a known method to generate a second intermediate compound 2*b*. After the reaction, as necessary, purification is performed by a known method such as column chromatography to obtain a second intermediate compound 2*b* having a side chain moiety for $R^2$ and a side chain moiety for $R^5$. As the order in which the first intermediate compound 1*a* or the first intermediate compound 1*b* is reacted, any of a halide having a protected hydroxy group corresponding to a side chain moiety for $R^2$ and a halide having a protected hydroxy group corresponding to a side chain moiety for $R^5$ may be reacted first.

As the halide having a protected hydroxy group corresponding to a side chain moiety for $R^2$ (or a side chain moiety for $R^5$) in Formula (1) used in the second reaction step, for example, compounds represented by the following Formulae (8-1) to (8-4) and the like can be used.

[Chem. 13]

(8-1)

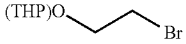

(8-2)

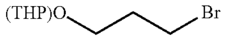

(8-3)

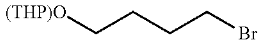

(8-4)

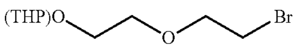

(in Formulae (8-1) to (8-4), THP represents a tetrahydropyranyl group).

Next, a deprotection reaction in which the protecting group derived from a halide having a protected hydroxy group, which the second intermediate compound 2*a* or the second intermediate compound 2*b* has, is removed by a known method depending on the type of protecting group is performed. Accordingly, one primary hydroxy group is arranged at the tips of a side chain moiety for $R^2$ and a side chain moiety for $R^5$ in Formula (1).

When the above step is performed, a fluorine-containing ether compound in which x in Formula (1) is 0 is obtained.

[Second Production Method]

When a fluorine-containing ether compound in which x in Formula (1) is 1 is produced, for example, the following second production method can be used.

(First Reaction Step)

<When Two $R^3$'s are the same and $R^1$ and $R^6$ are the Same>

When a compound in which, in Formula (1), x is 1, two $R^3$'s are the same, and $R^1$ and $R^6$ are the same is produced, first, in the same manner as in the first production method, a fluorine-based compound in which hydroxymethyl groups ($—CH_2OH$) are arranged at both terminals of a perfluoropolyether chain corresponding to $R^3$ in Formula (1) is prepared.

Next, among hydroxymethyl groups arranged at both terminals of the fluorine-based compound, a hydroxy group of one hydroxymethyl group is reacted with an epoxy compound corresponding to a group in which a group corresponding to $R^1$ and a group corresponding to a main chain moiety for $R^2$ in Formula (1) are bonded (=a group in which a group corresponding to $R^6$ and a group corresponding to a main chain moiety for $R^5$ are bonded). After the reaction, as necessary, purification is performed by a known method such as column chromatography to obtain a compound in which a hydroxymethyl group arranged at one terminal among hydroxymethyl groups arranged at both terminals of the fluorine-based compound is reacted with an epoxy compound.

According to the reaction, a precursor compound 11*a* having a group in which a group corresponding to $R^1$ and a group corresponding to a main chain moiety for $R^2$ are bonded (=a group in which a group corresponding to $R^6$ and a group corresponding to a main chain moiety for $R^5$ are bonded) at one terminal of a perfluoropolyether chain corresponding to $R^3$ is obtained. In the precursor compound 11*a*, in the group corresponding to a main chain moiety for $R^2$ (=group corresponding to a main chain moiety for $R^5$), one secondary hydroxy group generated by the reaction between the hydroxy group of the hydroxymethyl group and the epoxy group of the epoxy compound is arranged.

Next, the hydroxy group of the hydroxymethyl group arranged at one terminal of the precursor compound 11*a* is reacted with a halogen compound having an epoxy group corresponding to a main chain moiety for $R^4$ in Formula (1).

According to the reaction, a first intermediate compound 1*c* having a perfluoropolyether chain corresponding to $R^3$ at both ends of the structure corresponding to the main chain moiety for $R^4$ and also having a group in which a group corresponding to $R^1$ and a group corresponding to a main chain moiety for $R^2$ are bonded (=a group in which a group corresponding to $R^6$ and a group corresponding to a main chain moiety for $R^5$ are bonded) at the both ends is obtained. In the first intermediate compound 1*c*, in the group corresponding to the main chain moiety for $R^4$, one secondary hydroxy group generated by the reaction between the hydroxy group of the hydroxymethyl group and the epoxy group of the epoxy compound is arranged.

<When Two $R^3$'s are different and/or $R^1$ and $R^6$ are Different>

When a compound in which, in Formula (1), x is 1, two $R^3$'s are different and/or a compound in which $R^1$ and $R^6$ are different is produced, first, a fluorine-based compound in which hydroxymethyl groups ($—CH_2OH$) are arranged at both terminals of a perfluoropolyether chain corresponding to $R^3$ on the side of $R^1$ in Formula (1) is prepared. Then, a precursor compound 11*b* is produced in the same manner as in the production of the precursor compound 11*a* except that the fluorine-based compound is used.

The precursor compound 11*b* has a group in which a group corresponding to $R^1$ and a group corresponding to a main chain moiety for $R^2$ are bonded at one terminal of a perfluoropolyether chain corresponding to $R^3$ on the side of $R^1$. In the precursor compound 11*b*, in the group corresponding to a main chain moiety for R, one secondary hydroxy group generated by the reaction between the hydroxy group of the hydroxymethyl group and the epoxy group of the epoxy compound is arranged.

Next, a fluorine-based compound in which hydroxymethyl groups ($—CH_2OH$) are arranged at both terminals of a perfluoropolyether chain corresponding to $R^3$ on the side of $R^6$ in Formula (1) is prepared. Then, a hydroxy group of one hydroxymethyl group among hydroxymethyl groups arranged at both terminals of the fluorine-based compound is reacted with an epoxy compound corresponding to a group in which a group corresponding to $R^6$ and a group corresponding to a main chain moiety for $R^5$ are bonded in Formula (1). After the reaction, as necessary, purification is performed by a known method such as column chromatography to obtain a compound in which a hydroxymethyl group arranged at one terminal among hydroxymethyl groups arranged at both terminals of the fluorine-based compound is reacted with an epoxy compound.

According to the reaction, a precursor compound 11*c* having a group in which a group corresponding to $R^6$ and a group corresponding to a main chain moiety for $R^5$ are bonded at one terminal of a perfluoropolyether chain corresponding to $R^3$ on the side of $R^6$ is obtained. In the precursor compound 11*c*, in the group corresponding to a main chain moiety for $R^5$, one secondary hydroxy group generated by the reaction between the hydroxy group of the hydroxymethyl group and the epoxy group of the epoxy compound is arranged.

Next, a hydroxy group of a hydroxymethyl group arranged at one terminal of the precursor compound 11*b* is reacted with a halogen compound having an epoxy group corresponding to a main chain moiety for $R^4$ in Formula (1). Then, the obtained reaction product is reacted with a hydroxy group of a hydroxymethyl group arranged at one terminal of the precursor compound 11*c*. Here, a halogen compound having an epoxy group corresponding to a main chain moiety for $R^4$ in Formula (1) may be reacted with the precursor compound 11*c* and the obtained reaction product may be then reacted with the precursor compound 11*b*.

According to these reactions, a first intermediate compound 1*d* having a perfluoropolyether chain corresponding to $R^3$ on the side of $R^1$ at the end of the structure on the side of $R^1$ corresponding to a main chain moiety for $R^4$ and also having a group in which a group corresponding to $R^1$ and a group corresponding to a main chain moiety for $R^2$ are bonded at the end, and having a perfluoropolyether chain corresponding to $R^3$ on the side of $R^6$ at the end of the structure on the side of $R^6$ corresponding to a main chain moiety for $R^4$ and also having a group in which a group corresponding to $R^6$ and a group corresponding to a main chain moiety for $R^5$ are bonded at the end is obtained. In the first intermediate compound 1*d*, in the group corresponding to the main chain moiety for $R^4$, one secondary hydroxy group generated by the reaction between the hydroxy group of the hydroxymethyl group and the epoxy group is arranged.

As the halogen compound having an epoxy group corresponding to a main chain moiety for $R^4$ used in the first reaction step of the second production method, for example, epibromohydrin, epichlorohydrin, 2-bromoethyloxirane, 3-bromopropyloxirane, 2-chloroethyloxirane, 3-chloropropyloxirane and the like can be used, and when $R^4$ in Formula (1) is represented by Formula (3-1), and y1 and y2 in Formula (3-1) are both 1, or when $R^4$ is represented by Formula (3-2), and y3 and y4 in Formula (3-2) are both 1, for example, epibromohydrin or epichlorohydrin can be used.

As the epoxy compound corresponding to the group in which a group corresponding to $R^1$ and a group corresponding to a main chain moiety for $R^2$ in Formula (1) are bonded (or a group in which a group corresponding to $R^6$ and a group corresponding to a main chain moiety for $R^5$ are bonded) used in the first reaction step of the second production method, the same one as in the first production method can be used.

(Second Reaction Step)

<When Side Chain Moiety for $R^2$, side chain moiety for $R^4$ and side chain moiety for $R^5$ are the Same>

When a fluorine-containing ether compound in which, in Formula (1), x is 1, and a side chain moiety for $R^2$, a side chain moiety for $R^4$ and a side chain moiety for $R^5$ are the same is produced, in the second reaction step, one type of halide having a protected hydroxy group corresponding to a side chain moiety for $R^2$ (=a side chain moiety for $R^4$ and a side chain moiety for $R^5$) in Formula (1) is reacted with a secondary hydroxy group of the first intermediate compound 1*c* or the first intermediate compound 1*d* generated in the first reaction step to generate a second intermediate compound 2*c*.

<When Some or all of Side Chain Moiety for $R^2$, side chain moiety for $R^4$ and side chain moiety for $R^5$ are Different>

When a fluorine-containing ether compound in which, in Formula (1), x is 1, and some or all of a side chain moiety for $R^2$, a side chain moiety for $R^4$ and a side chain moiety for $R^5$ are different is produced, in the second reaction step, a halide having protected hydroxy groups corresponding to side chain moieties for $R^2$, $R^4$ and $R^5$ in Formula (1) is sequentially reacted with a secondary hydroxy group of the first intermediate compound 1*c* or first intermediate compound 1*d* generated in the first reaction step using a known method to generate a second intermediate compound 2*d*. After the reaction, as necessary, purification is performed by a known method such as column chromatography to obtain a second intermediate compound 2*d* having a side chain moiety for $R^2$, a side chain moiety for $R^4$ and a side chain moiety for $R^5$. The order in which a halide having protected hydroxy groups corresponding to side chain moieties for $R^2$, $R^4$ and $R^5$ is reacted with the first intermediate compound 1*c* or the first intermediate compound 1*d* is not particularly limited.

As the halide having protected hydroxy groups corresponding to side chain moieties for $R^2$, $R^4$ and $R^5$ in Formula (1) used in the second reaction step of the second production method, for example, the same halide having protected hydroxy groups corresponding to side chain moieties of $R^2$ and $R^5$ in Formula (1) that can be used in the first production method can be used.

Next, a deprotection reaction in which the protecting group derived from a halide having a protected hydroxy group, which the second intermediate compound 2*c* or the second intermediate compound 2*d* has, is removed by a known method depending on the type of protecting group is performed. Accordingly, one primary hydroxy group is arranged at the tips of a side chain moiety for $R^2$, a side chain moiety for $R^4$ and a side chain moiety for $R^5$ in Formula (1).

When the above step is performed, a fluorine-containing ether compound in which x in Formula (1) is 1 is obtained.

[Third Production Method]

When a fluorine-containing ether compound in which, in Formula (1), x is 2 is produced, for example, the following third production method can be used.

(First Reaction Step)

<When Three $R^3$'s are the same, two $R^4$'s are the same, and $R^1$ and $R^6$ are the Same>

When a compound in which, in Formula (1), x is 2, three $R^3$'s are the same, two $R^4$'s are the same, and $R^1$ and $R^6$ are the same is produced, first, a precursor compound 11*a* is produced in the same manner as in the second production method.

Next, a fluorine-based compound in which hydroxymethyl groups (—$CH_2OH$) are arranged at both terminals of a perfluoropolyether chain corresponding to $R^3$ in Formula (1) is prepared. Next, hydroxy groups of hydroxymethyl groups arranged at both terminals of the fluorine-based compound are reacted with a halogen compound having an epoxy group corresponding to a main chain moiety for $R^4$ in Formula (1). Accordingly, a precursor compound 11*d* having an epoxy group corresponding to a main chain moiety for $R^4$ at both terminals of a perfluoropolyether chain corresponding to $R^3$ in Formula (1) is obtained.

Then, a hydroxy group of a hydroxymethyl group arranged at one terminal of the precursor compound 11*a* is reacted with an epoxy group corresponding to a main chain moiety for $R^4$ arranged at both terminals of the precursor compound 11*d* to produce a first intermediate compound 1*e*. In the first intermediate compound 1*e*, in groups corresponding to main chain moieties for two $R^4$'s, one secondary hydroxy group generated by the reaction between the hydroxy group of the hydroxymethyl group and the epoxy group is arranged.

<When Two $R^4$'s are the same, some or all of three $R^3$'s are different, and/or $R^1$ and $R^6$ are Different>

When a compound in which, in Formula (1), x is 2, two $R^4$'s are the same, some or all of three $R^3$'s are different, and/or $R^1$ and $R^6$ are different is produced, the following method can be used.

That is, a precursor compound 11*e* is produced in the same manner as the precursor compound 11*d* except that, as the fluorine-based compound, a fluorine-based compound in which hydroxymethyl groups are arranged at both terminals of a perfluoropolyether chain corresponding to $R^3$ arranged in the center of the main chain among three $R^3$'s is used. The precursor compound 11*e* has an epoxy group corresponding to a main chain moiety for $R^4$ at both terminals of a perfluoropolyether chain corresponding to $R^3$ arranged in the center of the main chain among three $R^3$'s.

In addition, in the same manner as in the second production method, a precursor compound 11*b* and a precursor compound 11*c* are produced. Then, a hydroxy group of a hydroxymethyl group arranged at one terminal of the precursor compound 11*b* is reacted with an epoxy group corresponding to a main chain moiety for $R^4$ arranged at one terminal of the precursor compound 11*e*. The obtained reaction product is reacted with a hydroxy group of a hydroxymethyl group arranged at one terminal of the precursor compound 11*c* to produce a first intermediate compound 1*f*. Here, the precursor compound 11*e* may be reacted with the precursor compound 11*c*, and the obtained reaction product may be then reacted with the precursor compound 11*b*. In the first intermediate compound 1*f*, in groups corresponding to main chain moieties for two $R^4$'s, one secondary hydroxy group generated by the reaction between the hydroxy group of the hydroxymethyl group and the epoxy group is arranged.

<When Two $R^4$'s are Different>

When a compound in which, in Formula (1), x is 2, three $R^3$'s are the same, $R^1$ and $R^6$ are the same, and two $R^4$'s are different is produced, a first intermediate compound 1*e* is produced using the following precursor compound 11*f* in place of the precursor compound 11*d* having an epoxy group corresponding to a main chain moiety for $R^4$ at both terminals of a perfluoropolyether chain corresponding to $R^3$.

In addition, when a compound in which, in Formula (1), x is 2, some or all of three $R^3$'s are different, and/or $R^1$ and $R^6$ are different, and two $R^4$'s are different is produced, a first intermediate compound 1*f* is produced using the following precursor compound 11*f* in place of the precursor compound 11*e* having an epoxy group corresponding to a main chain moiety for $R^4$ at both terminals of a perfluoropolyether chain corresponding to $R^3$ arranged in the center of the main chain among three $R^3$'s.

The precursor compound 11*f* can be produced by the following method. That is, a fluorine-based compound in which hydroxymethyl groups are arranged at both terminals of a perfluoropolyether chain corresponding to $R^3$ (when some or all of three $R^3$'s are different, $R^3$ arranged in the center of the main chain among three $R^3$'s) is prepared. A hydroxy group of a hydroxymethyl group arranged at one terminal of the fluorine-based compound is reacted with a halogen compound having an epoxy group corresponding to a main chain moiety for $R^4$ on the side of $R^1$. Then, a hydroxy group of a hydroxymethyl group arranged at the other terminal of the fluorine-based compound is reacted with a halogen compound having an epoxy group corresponding to a main chain moiety for $R^4$ on the side of $R^6$.

Therefore, a precursor compound 11*f* having epoxy groups corresponding to main chain moieties for different $R^4$'s at both terminals of a perfluoropolyether chain corresponding to $R^3$ (when some or all of three $R^3$'s are different, $R^3$ arranged in the center of the main chain among three $R^3$'s) is obtained. As the order of reacting with the fluorine-based compound, any of a halogen compound having an epoxy group corresponding to a main chain moiety for $R^4$ on the side of $R^1$ and a halogen compound having an epoxy group corresponding to a main chain moiety for $R^4$ on the side of $R^6$ may be reacted first.

As the halogen compound having epoxy groups corresponding to main chain moieties for $R^4$ on the side of $R^1$ and for $R^4$ on the side of $R^6$ used in the first reaction step of the third production method, the same halogen compound having an epoxy group corresponding to a main chain moiety for $R^4$ used in the first reaction step of the second production method can be used.

As the halogen compound having an epoxy group corresponding to a main chain moiety for $R^4$ on the side of $R^1$, for example, when $R^4$ on the side of $R^1$ is represented by Formula (3-1), and in Formula (3-1), y1 is 1 and y2 is 2, or when $R^4$ on the side of $R^1$ is represented by Formula (3-2), and in Formula (3-2), y3 is 1 and y4 is 2,2-chloroethyloxirane or 2-bromoethyloxirane can be used. In addition, when $R^4$ on the side of $R^1$ is represented by Formula (3-1), and in Formula (3-1), y1 is 1 and y2 is 3 or when $R^4$ on the side of $R^1$ is represented by Formula (3-2), and in Formula (3-2), y3 is 1 and y4 is 3,3-chloropropyloxirane, or 3-bromopropyloxirane can be used.

As the halogen compound having an epoxy group corresponding to a main chain moiety for $R^4$ on the side of $R^6$, for example, when $R^4$ on the side of $R^6$ is represented by Formula (3-1), and in Formula (3-1), y1 is 2 and y2 is 1, or when $R^4$ on the side of $R^6$ is represented by Formula (3-2), and in Formula (3-2), y3 is 2 and y4 is 1,2-chloroethyloxirane or 2-bromoethyloxirane can be used. In addition, when $R^4$ on the side of $R^6$ is represented by Formula (3-1), and in Formula (3-1), y1 is 3 and y2 is 1, or when $R^4$ on the side of $R^6$ is represented by Formula (3-2), and in Formula (3-2), y3 is 3 and y4 is 1,3-chloropropyloxirane or 3-bromopropyloxirane can be used.

(Second Reaction Step)

<When Side Chain Moiety for $R^2$, side chain moieties for two $R^4$'s, and Side Chain Moiety For $R^5$ are the Same>

When a fluorine-containing ether compound in which, in Formula (1), x is 2, and a side chain moiety for $R^2$, side chain moieties for two $R^4$'s and a side chain moiety for $R^5$ are the same is produced, in the second reaction step, one type of halide having a protected hydroxy group corresponding to a side chain moiety for $R^2$ (=side chain moieties for two $R^4$'s and a side chain moiety for $R^5$) in Formula (1) is reacted with a secondary hydroxy group of the first intermediate compound 1*e* or the first intermediate compound 1*f* generated in the first reaction step to generate a second intermediate compound 2*e*.

<When Some or all of Side Chain Moiety for $R^2$, side chain moieties for two $R^4$'s and side chain moiety for $R^5$ are Different>

When a fluorine-containing ether compound in which, in Formula (1), x is 2, and some or all of a side chain moiety for $R^2$, side chain moieties for two $R^4$'s, and a side chain moiety for $R^5$ are different is produced, in the second reaction step, a halide having protected hydroxy groups corresponding to side chain moieties for $R^2$, two $R^4$'s and $R^5$ in Formula (1) is sequentially reacted with a secondary hydroxy group of the first intermediate compound 1*e* or the first intermediate compound 1*f* generated in the first reaction step using a known method to generate a second intermediate compound 2*f*. After the reaction, as necessary, purification is performed by a known method such as column chromatography to obtain a second intermediate compound 2*f* having a side chain moiety for $R^2$, side chain moieties for two $R^4$'s and a side chain moiety for $R^5$. The order in which the halide having protected hydroxy groups corresponding to side chain moieties for $R^2$, two $R^4$'s and $R^5$ is reacted with the first intermediate compound 1*e* or the first intermediate compound 1*f* is not particularly limited.

As the halide having protected hydroxy groups corresponding to side chain moieties for $R^2$, two $R^4$'s and $R^5$ in Formula (1) used in the second reaction step of the third production method, for example, the same halide having protected hydroxy groups corresponding to side chain moieties for $R^2$, $R^4$ and $R^5$ in Formula (1) that can be used in the second production method can be used.

Next, a deprotection reaction in which the protecting group derived from a halide having a protected hydroxy group, which the second intermediate compound 2*e* or the second intermediate compound 2*f* has, is removed by a known method depending on the type of protecting group. Accordingly, one primary hydroxy group is arranged at the tips of a side chain moiety for $R^2$, side chain moieties for two $R^4$'s and a side chain moiety for $R^5$ in Formula (1).

When the above step is performed, a fluorine-containing ether compound in which x in Formula (1) is 2 is obtained.

[Lubricant for Magnetic Recording Medium]

The lubricant for magnetic recording medium of the present embodiment contains the fluorine-containing ether compound represented by Formula (1).

The lubricant of the present embodiment can be used by being mixed with a known material used as a material for the lubricant as necessary as long as the characteristics are not impaired due to the inclusion of the fluorine-containing ether compound represented by Formula (1).

Specific examples of known materials include, for example, FOMBLIN (registered trademark) ZDIAC, FOMBLIN ZDEAL, and FOMBLIN AM-2001 (all commercially available from Solvay Solexis), and Moresco A20H (commercially available from Moresco). A known material used in combination with the lubricant of the present embodiment preferably has a number-average molecular weight of 1,000 to 10,000.

When the lubricant of the present embodiment contains a material other than the fluorine-containing ether compound represented by Formula (1), the content of the fluorine-containing ether compound represented by Formula (1) in the lubricant of the present embodiment is preferably 50 mass % or more and more preferably 70 mass % or more.

Since the lubricant of the present embodiment contains the fluorine-containing ether compound represented by Formula (1), it is possible to form a lubricating layer having favorable chemical substance resistance and a strong pickup minimizing effect.

[Magnetic Recording Medium]

In a magnetic recording medium of the present embodiment, at least a magnetic layer, a protective layer, and a lubricating layer are sequentially provided on a substrate.

In the magnetic recording medium of the present embodiment, as necessary, one, two or more base layers can be provided between the substrate and the magnetic layer. In addition, at least one of the adhesive layer and the soft magnetic layer can be provided between the base layer and the substrate.

The FIGURE is a schematic cross-sectional view showing a magnetic recording medium according to one embodiment of the present invention.

A magnetic recording medium 10 of the present embodiment has a structure in which an adhesive layer 12, a soft magnetic layer 13, a first base layer 14, a second base layer 15, a magnetic layer 16, a protective layer 17, and a lubricating layer 18 are sequentially provided on a substrate 11.

"Substrate"

As the substrate 11, for example, a non-magnetic substrate in which a film made of NiP or a NiP alloy is formed on a base made of a metal or an alloy material such as Al or an Al alloy can be used.

In addition, as the substrate 11, a non-magnetic substrate made of a non-metallic material such as glass, a ceramic, silicon, silicon carbide, carbon, and a resin may be used, or a non-magnetic substrate in which a film of NiP or a NiP alloy is formed on a base made of these non-metallic materials may be used.

"Adhesive Layer"

The adhesive layer 12 prevents the progress of corrosion of the substrate 11 that occurs when the substrate 11 and the soft magnetic layer 13 provided on the adhesive layer 12 are arranged in contact with each other.

The material of the adhesive layer 12 can be appropriately selected from among, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 preferably has a structure in which a first soft magnetic film, an intermediate layer made of a Ru film, and a second soft magnetic film are sequentially laminated. That is, the soft magnetic layer 13 preferably has a structure in which an intermediate layer made of a Ru film is interposed between two soft magnetic film layers, and thus the soft magnetic films above and below the intermediate layer are bonded by anti-ferromagnetic coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Thereby, the amorphization of the first soft magnetic film and the second soft magnetic film is promoted. As a result, the orientation of the first base layer (seed layer) can be improved, and the raised amount of the magnetic head can be reduced.

The soft magnetic layer 13 can be formed by, for example, a sputtering method.

"First Base Layer"

The first base layer 14 is a layer that controls the orientation and the crystal size of the second base layer 15 and the magnetic layer 16 provided thereon.

Examples of the first base layer 14 include a Cr layer, a Ta layer, a Ru layer, a CrMo alloy layer, a CoW alloy layer, a CrW alloy layer, a CrV alloy layer, and a CrTi alloy layer.

The first base layer 14 can be formed by, for example, a sputtering method.

"Second Base Layer"

The second base layer 15 is a layer that controls the orientation of the magnetic layer 16 such that it becomes favorable. The second base layer 15 is preferably a layer made of Ru or a Ru alloy.

The second base layer 15 may be a single layer or may be composed of a plurality of layers. When the second base layer 15 is composed of a plurality of layers, all of the layers may be composed of the same material, or at least one layer may be composed of a different material.

The second base layer 15 can be formed by, for example, a sputtering method.

"Magnetic Layer"

The magnetic layer 16 is made of a magnetic film in which the axis of easy magnetization is in a direction perpendicular or horizontal to the surface of the substrate. The magnetic layer 16 is a layer containing Co and Pt. The magnetic layer 16 may be a layer containing an oxide, Cr, B, Cu, Ta, Zr or the like in order to improve SNR characteristics.

Examples of oxides contained in the magnetic layer 16 include $SiO_2$, SiO, $Cr_2O_3$, CoO, $Ta_2O_3$, and $TiO_2$.

The magnetic layer 16 may be composed of one layer or may be composed of a plurality of magnetic layers made of materials with different compositions.

For example, when the magnetic layer 16 is composed of three layers including a first magnetic layer, a second magnetic layer and a third magnetic layer sequentially laminated from below, the first magnetic layer preferably has a granular structure made of a material containing Co, Cr, and Pt, and further containing an oxide. As the oxide contained in the first magnetic layer, for example, it is preferable to use an oxide of Cr, Si, Ta, Al, Ti, Mg, Co or the like. Among these, particularly, $TiO_2$, $Cr_2O_3$, $SiO_2$ or the like can be preferably used. In addition, the first magnetic layer is preferably made of a composite oxide in which two or more oxides are added. Among these, particularly, $Cr_2O_3$—$SiO_2$, $Cr_2O_3$—$TiO_2$, $SiO_2$—$TiO_2$ or the like can be preferably used.

The first magnetic layer can contain one or more elements selected from among B, Ta, Mo, Cu, Nd, W, Nb, Sm, Tb, Ru, and Re in addition to Co, Cr, Pt, and an oxide. For the second magnetic layer, the same material as for the first magnetic layer can be used. The second magnetic layer preferably has a granular structure.

The third magnetic layer preferably has a non-granular structure made of a material containing Co, Cr, and Pt and not containing an oxide. The third magnetic layer can contain one or more elements selected from among B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a non-magnetic layer between adjacent magnetic layers. When the magnetic layer 16 is composed of three layers including a first magnetic layer, a second magnetic layer and a third magnetic layer, it is preferable to provide a non-magnetic layer between the first magnetic layer and the second magnetic layer and between the second magnetic layer and the third magnetic layer.

For the non-magnetic layer provided between adjacent magnetic layers of the magnetic layer 16, for example, Ru, a Ru alloy, a CoCr alloy, a CoCrX1 alloy (X1 represents one, two or more elements selected from among Pt, Ta, Zr, Re, Ru, Cu, Nb, Ni, Mn, Ge, Si, O, N, W, Mo, Ti, V, and B) or the like can be preferably used.

For the non-magnetic layer provided between adjacent magnetic layers of the magnetic layer 16, it is preferable to use an alloy material containing an oxide, a metal nitride, or a metal carbide. Specifically, as the oxide, for example, $SiO_2$, $Al_2O_3$, $Ta_2O_5$, $Cr_2O_3$, MgO, $Y_2O_3$, $TiO_2$ or the like can be used. As the metal nitride, for example, AlN, $Si_3N_4$, TaN, CrN or the like can be used. As the metal carbide, for example, TaC, BC, SiC or the like can be used.

The non-magnetic layer can be formed by, for example, a sputtering method.

The magnetic layer 16 is preferably a magnetic layer for perpendicular magnetic recording in which the axis of easy magnetization is in a direction perpendicular to the surface of the substrate in order to realize a higher recording density. The magnetic layer 16 may be a magnetic layer for in-plane magnetic recording.

The magnetic layer 16 may be formed by any conventionally known method such as a vapor deposition method, an ion beam sputtering method, and a magnetron sputtering method. The magnetic layer 16 is generally formed by a sputtering method.

"Protective Layer"

The protective layer 17 protects the magnetic layer 16. The protective layer 17 may be composed of one layer or may be composed of a plurality of layers. As the protective layer 17, a carbon-based protective layer can be preferably used, and an amorphous carbon protective layer is particularly preferable. When the protective layer 17 is a carbon-based protective layer, this is preferable because the interaction with the polar group (particularly the hydroxy group) contained in the fluorine-containing ether compound in the lubricating layer 18 is further improved.

The adhesive force between the carbon-based protective layer and the lubricating layer 18 can be controlled by forming a carbon-based protective layer with hydrogenated carbon and/or nitrogenated carbon, and adjusting the hydrogen content and/or nitrogen content in the carbon-based protective layer. The hydrogen content in the carbon-based protective layer measured by a hydrogen forward scattering (HFS) is preferably 3 atom % to 20 atom %. In addition, the nitrogen content in the carbon-based protective layer measured through X-ray photoelectron spectroscopy (XPS) is preferably 4 atom % to 15 atom %.

Hydrogen and/or nitrogen contained in the carbon-based protective layer need not be uniformly contained through the entire carbon-based protective layer. For example, the carbon-based protective layer is preferably formed as a composition gradient layer in which nitrogen is contained in the protective layer 17 on the side of the lubricating layer 18 and hydrogen is contained in the protective layer 17 on the side of the magnetic layer 16. In this case, the adhesive force between the magnetic layer 16 and the lubricating layer 18, and the carbon-based protective layer is further improved.

The film thickness of the protective layer 17 is preferably 1 nm to 7 nm. When the film thickness of the protective layer 17 is 1 nm or more, the performance of the protective layer 17 can be sufficiently obtained. The film thickness of the protective layer 17 is preferably 7 nm or less in order to reduce the thickness of the protective layer 17.

As a film formation method for the protective layer 17, a sputtering method using a target material containing carbon, a chemical vapor deposition (CVD) method using a hydrocarbon raw material such as ethylene or toluene, an ion beam deposition (IBD) method or the like can be used.

When a carbon-based protective layer is formed as the protective layer 17, for example, a film can be formed by a DC magnetron sputtering method. Particularly, when a carbon-based protective layer is formed as the protective layer 17, it is preferable to form an amorphous carbon protective layer by a plasma CVD method. The amorphous carbon protective layer formed by the plasma CVD method has a uniform surface and low roughness.

"Lubricating Layer"

The lubricating layer 18 prevents contamination of the magnetic recording medium 10. In addition, the lubricating layer 18 reduces a frictional force of a magnetic head of a magnetic recording and reproducing device, which slides on the magnetic recording medium 10, and improves the durability of the magnetic recording medium 10.

As shown in the FIGURE, the lubricating layer 18 is formed on and in contact with the protective layer 17. The lubricating layer 18 is formed by applying the lubricant for magnetic recording medium according to the embodiment described above to the protective layer 17. Therefore, the lubricating layer 18 contains the above fluorine-containing ether compound.

When the protective layer 17 arranged below the lubricating layer 18 is a carbon-based protective layer, particularly, the lubricating layer 18 is bonded to the protective layer 17 with a bonding force. As a result, even if the thickness of the lubricating layer 18 is thin, it is easy to obtain the magnetic recording medium 10 in which the surface of the protective layer 17 is covered at a high coating rate, and it is possible to effectively prevent contamination of the surface of the magnetic recording medium 10.

The average film thickness of the lubricating layer 18 is preferably 0.5 nm (5 Å) to 2.0 nm (20 Å) and more preferably 0.5 nm (5 Å) to 1.2 nm (12 Å). When the average film thickness of the lubricating layer 18 is 0.5 nm or more, the lubricating layer 18 is formed with a uniform film thickness without forming an island shape or a mesh shape. Therefore, the surface of the protective layer 17 can be coated with the lubricating layer 18 at a high coating rate. In addition, when the average film thickness of the lubricating layer 18 is 2.0 nm or less, the lubricating layer 18 can be made sufficiently thin, and the raised amount of the magnetic head can be sufficiently reduced.

"Method of Forming Lubricating Layer"

Examples of methods of forming the lubricating layer 18 include a method in which a magnetic recording medium during production in which respective layers up to the protective layer 17 are formed on the substrate 11 is prepared, and a lubricating layer forming solution is applied onto the protective layer 17.

The lubricating layer forming solution can be obtained by dispersing and dissolving the lubricant for magnetic recording medium according to the embodiment described above in a solvent as necessary, and adjusting the viscosity and concentration to be suitable for application methods.

Examples of solvents used for the lubricating layer forming solution include fluorine-based solvents such as Vertel (registered trademark) XF (product name, commercially available from Du Pont-Mitsui Fluorochemicals Co., Ltd.).

The method of applying a lubricating layer forming solution is not particularly limited, and examples thereof include a spin coating method, a spraying method, a paper coating method, and a dipping method.

When the dipping method is used, for example, the following method can be used. First, the substrate 11 in which respective layers up to the protective layer 17 are formed is immersed in the lubricating layer forming solution contained in an immersion tank of a dip coating device. Next, the substrate 11 is lifted from the immersion tank at a predetermined speed. Accordingly, the lubricating layer forming solution is applied to the surface of the protective layer 17 of the substrate 11.

When the dipping method is used, the lubricating layer forming solution can be uniformly applied to the surface of the protective layer 17, and the lubricating layer 18 with a uniform film thickness can be formed on the protective layer 17.

In the present embodiment, the substrate 11 in which the lubricating layer 18 is formed is preferably subjected to a heat treatment. When the heat treatment is performed, the adhesion between the lubricating layer 18 and the protective layer 17 is improved, and the adhesive force between the lubricating layer 18 and the protective layer 17 is improved.

The heat treatment temperature is preferably 100° C. to 180° C. and more preferably 100° C. to 160° C. When the heat treatment temperature is 100° C. or higher, an effect of improving the adhesion between the lubricating layer 18 and the protective layer 17 is sufficiently obtained. In addition, when the heat treatment temperature is 180° C. or lower, it is possible to prevent thermal decomposition of the lubricating layer 18 according to the heat treatment. The heat treatment time can be appropriately adjusted according to the heat treatment temperature, and is preferably 10 minutes to 120 minutes.

In the present embodiment, in order to further improve the adhesive force of the lubricating layer 18 with respect to the protective layer 17, an ultraviolet ray (UV) emitting treatment may be performed on the lubricating layer 18 before the heat treatment or after the heat treatment.

In the magnetic recording medium 10 of the present embodiment, at least the magnetic layer 16, the protective layer 17, and the lubricating layer 18 are sequentially provided on the substrate 11. In the magnetic recording medium 10 of the present embodiment, the lubricating layer 18 containing the above fluorine-containing ether compound is formed on and in contact with the protective layer 17. The lubricating layer 18 has favorable chemical substance resistance and a strong pickup minimizing effect. Accordingly, the magnetic recording medium 10 of the present embodiment has excellent reliability, and particularly has an excellent silicon contamination minimization ability and durability. Therefore, the magnetic recording medium 10 of the present embodiment can have a small raised amount of the magnetic head (for example, 10 nm or less), and operates stably for a long period of time even in a harsh environment due to diversity of applications. Therefore, the magnetic recording medium 10 of the present embodiment is particularly preferable as a magnetic disk mounted in a load unload (LUL) type magnetic disk device.

EXAMPLES

Hereinafter, the present invention will be described in more detail with reference to examples and comparative examples. Here, the present invention is not limited only to the following examples.

Example 1

The compound represented by Formula (A) was obtained by the following method.

(First Reaction Step)

10 g of a compound (a number-average molecular weight of 1,000 and a molecular weight distribution of 1.1) represented by $HOCH_2CF_2O(CF_2CF_2O)_h(CF_2O)_iCF_2CH_2OH$ (in the formula, h indicating an average degree of polymerization is 4.5, and i indicating an average degree of polymerization is 4.5), 4.75 g of the compound represented by Formula (7-1), and 20 mL of t-butanol were put into 100 mL eggplant flask under a nitrogen gas atmosphere, and stirred at room temperature until they became uniform to form a mixture. 0.90 g of potassium tert-butoxide was added to the mixture, and the mixture was stirred and reacted at 70° C. for 16 hours.

The compound represented by Formula (7-1) was synthesized by a method of protecting a hydroxy group of 3-buten-1-ol using dihydropyran and then performing oxidization with m-chloroperbenzoic acid.

The reaction product obtained after the reaction was cooled to 25° C., transferred into a separatory funnel containing 100 mL of water, and extracted three times with 100 mL of ethyl acetate. The organic layer was washed with water and dehydrated with anhydrous sodium sulfate. After the desiccant was filtered, the filtrate was concentrated, and the residue was purified through silica gel column chromatography to obtain 11.31 g of a compound represented by the following Formula (9) as a first intermediate compound.

[Chem. 14]

(9)

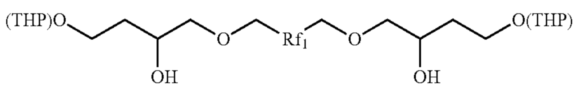

(in Formula (9), $Rf_1$ is the PFPE chain represented by Formula (4-1); in $Rf_1$, h indicating an average degree of polymerization represents 4.5 and i indicating an average degree of polymerization represents 4.5; and THP represents a tetrahydropyranyl group).

(Second Reaction Step)

Subsequently, 11.31 g of the compound represented by Formula (9) as the first intermediate compound obtained above, 4.09 g of the compound represented by Formula (8-1) (2-(2-bromoethoxy)tetrahydro-2H-pyran), and 20 mL of dimethylformamide were put into 100 mL eggplant flask under a nitrogen gas atmosphere, and stirred at room temperature until they became uniform. 0.78 g of sodium hydride was added to the uniform solution, and the mixture was stirred and reacted at 40° C. for 16 hours.

The reaction solution obtained after the reaction was returned to room temperature, 5 g of a 10% hydrogen chloride/methanol solution (a hydrogen chloride-methanol reagent (5-10%), commercially available from Tokyo Chemical Industry Co., Ltd.) was added, and the mixture was stirred at room temperature for 4 hours. Then, the reaction solution was transferred little by little into a separatory funnel containing 100 mL of a saturated sodium bicarbonate solution, and extracted with twice with 200 mL of ethyl acetate. The organic layer was washed with 100 mL of a saline solution, 100 mL of a saturated sodium bicarbonate solution, and 100 mL of a saline solution in that order, and dehydrated with anhydrous sodium sulfate. After the desiccant was filtered, the filtrate was concentrated, and the residue was purified through silica gel column chromatography to obtain 4.15 g of a compound (A) (in Formula (A), $Rf_1$ is the PFPE chain represented by Formula (4-1), and in $Rf_1$, h indicating an average degree of polymerization represents 4.5 and i indicating an average degree of polymerization represents 4.5).

The obtained compound (A) was subjected to $^1$H-NMR and $^{19}$F-NMR measurement, and the structure was identified based on the following results.

$^1$H-NMR (acetone-$D_6$): δ[ppm]=1.60-1.80 (4H), 3.40-3.85 (22H), 3.85-4.10 (4H)

$^{19}$F-NMR (acetone-$D_6$): δ[ppm]=−55.5 to −51.5 (9F), −78.5 (2F), −80.5 (2F), −91.0 to −88.5 (18F)

Example 2

The compound represented by Formula (B) was obtained by the following method.

4.02 g of the compound (B) (in Formula (B), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that a compound represented by Formula (7-2) was used in place of the compound represented by Formula (7-1).

The compound represented by Formula (7-2) was synthesized by a method of protecting a hydroxy group of an allyl alcohol using dihydropyran and then performing oxidization with m-chloroperbenzoic acid.

The obtained compound (B) was subjected to $^1$H-NMR and $^{19}$F-NMR measurement, and the structure was identified based on the following results.

$^1$H-NMR (acetone-$D_6$): δ[ppm]=3.40-3.85 (22H), 3.85-4.10 (4H)

$^{19}$F-NMR (acetone-$D_6$): δ[ppm]=−55.5 to −51.5 (9F), −78.5 (2F), −80.5 (2F), −91.0 to −88.5 (18F)

Example 3

The compound represented by Formula (C) was obtained by the following method.

4.81 g of the compound (C) (in Formula (C), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that a compound represented by Formula (7-3) was used in place of the compound represented by Formula (7-1).

The compound represented by Formula (7-3) was synthesized by a method of protecting a hydroxy group of ethylene glycol monoallyl ether using dihydropyran and then performing oxidization with m-chloroperbenzoic acid.

The obtained compound (C) was subjected to $^1$H-NMR and $^{19}$F-NMR measurement, and the structure was identified based on the following results.

$^1$H-NMR (acetone-$D_6$): δ[ppm]=3.40-3.85 (34H), 3.85-4.10 (4H)

$^{19}$F-NMR (acetone-$D_6$): δ[ppm]=−55.5 to −51.5 (9F), −78.5 (2F), −80.5 (2F), −91.0 to −88.5 (18F)

Example 4

The compound represented by Formula (D) was obtained by the following method.

5.21 g of the compound (D) (in Formula (D), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that a compound represented by Formula (7-4) was used in place of the compound represented by Formula (7-1).

The compound represented by Formula (7-4) was synthesized by the following method. One hydroxy group of ethylene glycol was protected using dihydropyran and then reacted with allyl glycidyl ether. The secondary hydroxy group generated after the reaction was protected using methoxymethyl chloride and oxidization was then performed with m-chloroperbenzoic acid for synthesis.

The obtained compound (D) was subjected to $^1$H-NMR and $^{19}$F-NMR measurement, and the structure was identified based on the following results.

$^1$H-NMR (acetone-$D_6$): δ[ppm]=3.40-3.85 (34H), 3.85-4.10 (4H)

$^{19}$F-NMR (acetone-$D_6$): δ[ppm]=−55.5 to −51.5 (9F), −78.5 (2F), −80.5 (2F), −91.0 to −88.5 (18F)

Example 5

The compound represented by Formula (E) was obtained by the following method.

5.41 g of the compound (E) (in Formula (E), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (7-1), a compound represented by Formula (7-5) was used.

The compound represented by Formula (7-5) was synthesized by the following method. Epichlorohydrin was reacted with a molar amount of twice that of allyl alcohol. The secondary hydroxy group generated after the reaction was protected using methoxymethyl chloride and one carbon-carbon double bond was then oxidized with m-chloroperbenzoic acid for synthesis.

The obtained compound (E) was subjected to $^1$H-NMR and $^{19}$F-NMR measurement, and the structure was identified based on the following results.

$^1$H-NMR (acetone-$D_6$): δ[ppm]=3.40-3.85 (36H), 3.85-4.10 (4H), 5.2-6.1 (6H)

$^{19}$F-NMR (acetone-$D_6$): δ[ppm]=−55.5 to −51.5 (9F), −78.5 (2F), −80.5 (2F), −91.0 to −88.5 (18F)

Example 6

The compound represented by Formula (F) was obtained by the following method.

5.82 g of the compound (F) (in Formula (F), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (7-1), a compound represented by Formula (7-6) was used.

The compound represented by Formula (7-6) was synthesized by the following method. Phenol was reacted with allyl glycidyl ether. The secondary hydroxy group generated after the reaction was protected using methoxymethyl chloride, and oxidization was performed with m-chloroperbenzoic acid for synthesis.

The obtained compound (F) was subjected to $^{1}H$-NMR and $^{19}F$-NMR measurement, and the structure was identified based on the following results.

$^{1}H$-NMR (acetone-$D_6$): δ[ppm]=3.40-3.85 (32H), 3.85-4.10 (4H), 6.8-7.6 ppm (10H)

$^{19}F$-NMR (acetone-$D_6$): δ[ppm]=−55.5 to −51.5 (9F), −78.5 (2F), −80.5 (2F), −91.0 to −88.5 (18F)

Example 7

The compound represented by Formula (G) was obtained by the following method.

4.61 g of the compound (G) (in Formula (G), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (7-1), a compound represented by Formula (7-7) was used.

The compound represented by Formula (7-7) was synthesized by reacting 3-cyanopropanol with epibromohydrin.

The obtained compound (G) was subjected to $^{1}H$-NMR and $^{19}F$-NMR measurement, and the structure was identified based on the following results.

$^{1}H$-NMR (acetone-$D_6$): δ[ppm]=1.60-1.80 (4H), 2.00-2.10 (4H), 3.40-3.85 (24H), 3.85-4.10 (4H)

$^{19}F$-NMR (acetone-$D_6$): δ[ppm]=−55.5 to −51.5 (9F), −78.5 (2F), −80.5 (2F), −91.0 to −88.5 (18F)

Example 8

The compound represented by Formula (H) was obtained by the following method.

4.33 g of the compound (H) (in Formula (H), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (7-1), a compound represented by Formula (7-8) was used.

The compound represented by Formula (7-8) was synthesized by reacting acetaminoethanol with epibromohydrin.

The obtained compound (H) was subjected to $^{1}H$-NMR and $^{19}F$-NMR measurement, and the structure was identified based on the following results.

$^{1}H$-NMR (acetone-$D_6$): δ[ppm]=1.90-2.00 (6H), 3.40-3.85 (24H), 3.85-4.10 (4H), 6.30-6.40 (2H)

$^{19}F$-NMR (acetone-$D_6$): δ[ppm]=−55.5 to −51.5 (9F), −78.5 (2F), −80.5 (2F), −91.0 to −88.5 (18F)

Example 9

The compound represented by Formula (I) was obtained by the following method.

4.18 g of the compound (I) (in Formula (I), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (8-1), a compound represented by Formula (8-2) was used.

The compound represented by Formula (8-2) was synthesized by protecting a hydroxy group of 3-bromopropanol using dihydropyran.

The obtained compound (I) was subjected to $^{1}H$-NMR and $^{19}F$-NMR measurement, and the structure was identified based on the following results.

$^{1}H$-NMR (acetone-$D_6$): δ[ppm]=1.60-1.80 (8H), 3.45-3.85 (22H), 3.85-4.10 (4H)

$^{19}F$-NMR (acetone-$D_6$): δ[ppm]=−55.5 to −51.5 (9F), −78.5 (2F), −80.5 (2F), −91.0 to −88.5 (18F)

Example 10

The compound represented by Formula (J) was obtained by the following method.

4.36 g of the compound (J) (in Formula (J), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (8-1), a compound represented by Formula (8-3) was used.

The compound represented by Formula (8-3) was synthesized by protecting a hydroxy group of 4-bromobutanol using dihydropyran.

The obtained compound (J) was subjected to $^{1}H$-NMR and $^{19}F$-NMR measurement, and the structure was identified based on the following results.

$^{1}H$-NMR (acetone-$D_6$): δ[ppm]=1.60-1.80 (12H), 3.45-3.85 (22H), 3.85-4.10 (4H)

$^{19}F$-NMR (acetone-$D_6$): δ[ppm]=−55.5 to −51.5 (9F), −78.5 (2F), −80.5 (2F), −91.0 to −88.5 (18F)

Example 11

The compound represented by Formula (K) was obtained by the following method.

4.54 g of the compound (K) (in Formula (K), $Rf_1$ is the PFPE chain represented by Formula (4-1), and in $Rf_1$, h indicating an average degree of polymerization represents 4.5 and i indicating an average degree of polymerization represents 4.5) was obtained in the same operation as in Example 1 except that, in place of the compound represented by Formula (8-1), a compound represented by Formula (8-4) was used.

The compound represented by Formula (8-4) was synthesized by brominating one hydroxy group of diethylene glycol using phosphorus tribromide and then protecting the other hydroxy group using dihydropyran.

The obtained compound (K) was subjected to $^{1}H$-NMR and $^{19}F$-NMR measurement, and the structure was identified based on the following results.

$^{1}H$-NMR (acetone-$D_6$): δ[ppm]=1.60-1.80 (4H), 3.45-3.85 (30H), 3.85-4.10 (4H)

$^{19}F$-NMR (acetone-$D_6$): δ[ppm]=−55.5 to −51.5 (9F), −78.5 (2F), −80.5 (2F), −91.0 to −88.5 (18F)

Example 12

The compound represented by Formula (L) was obtained by the following 4.26 g of the compound (L) (in Formula (L), $Rf_2$ is the PFPE chain represented by Formula (4-2), and in $Rf_2$, j indicating an average degree of polymerization represents 4.5) was obtained in the same operation as in Example 1 except that, in place of the compound represented by $HOCH_2CF_2O(CF_2CF_2O)$ n $(CF_2O)_iCF_2CH_2OH$, a compound (a number-average molecular weight of 1,000 and a molecular weight distribution of 1.1) represented by $HOCH_2CF_2CF_2O(CF_2CF_2CF_2O)_jCF_2CF_2CH_2OH$ (in the formula, j indicating an average degree of polymerization is 4.5) was used.

The obtained compound (L) was subjected to $^1H$-NMR and $^{19}F$-NMR measurement, and the structure was identified based on the following results.

$^1H$-NMR (acetone-$D_6$): δ[ppm]=1.60-1.80 (4H), 3.45-3.85 (30H), 3.85-4.10 (4H)

$^{19}F$-NMR (acetone-$D_6$): δ[ppm]=−84.0 to −83.0 (18F), −86.4 (4F), −124.3 (4F), −130.0 to −129.0 (9F)

Example 13

The compound represented by Formula (M) was obtained by the following method.

4.10 g of the compound (M) (in Formula (M), $Rf_3$ is the PFPE chain represented by Formula (4-3), and in $Rf_3$, k indicating an average degree of polymerization represents 3.0) was obtained in the same operation as in Example 1 except that, in place of the compound represented by $HOCH_2CF_2O(CF_2CF_2O)$ n $(CF_2O)_iCF_2CH_2OH$, a compound (a number-average molecular weight of 1,000 and a molecular weight distribution of 1.1) represented by $HOCH_2CF_2CF_2CF_2O(CF_2CF_2CF_2CF_2O)_kCF_2CF_2CF_2$ $CH_2OH$ (in the formula, k indicating an average degree of polymerization is 3.0) was used.

The obtained compound (M) was subjected to $^1H$-NMR and $^{19}F$-NMR measurement, and the structure was identified based on the following results.

$^1H$-NMR (acetone-$D_6$): δ[ppm]=1.60-1.80 (4H), 3.45-3.85 (30H), 3.85-4.10 (4H)

$^{19}F$-NMR (acetone-$D_6$): δ[ppm]=−84.0 to −83.0 (16F), −122.5 (4F), −126.0 (12F), −129.0 to −128.0 (4F)

Example 14

The compound represented by Formula (N) was obtained by the following method.

[Chem. 16]

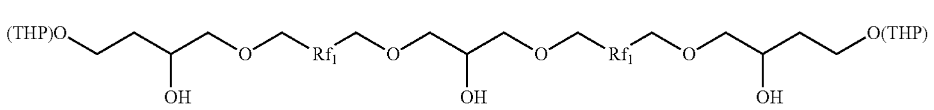

(11)

(First Reaction Step)

20 g of the compound (a number-average molecular weight of 1,000 and a molecular weight distribution of 1.1) represented by $HOCH_2CF_2O(CF_2CF_2O)$ n $(CF_2O)_iCF_2CH_2OH$ (in the formula, h indicating an average degree of polymerization is 4.5, and i indicating an average degree of polymerization is 4.5), 2.06 g of the compound represented by Formula (7-1), and 20 mL of t-butanol were put into 100 mL eggplant flask under a nitrogen gas atmosphere, and stirred at room temperature until they became uniform to form a mixture. 0.90 g of potassium tert-butoxide was added to the mixture, and the mixture was stirred and reacted at 70° C. for 16 hours.

The reaction product obtained after the reaction was cooled to 25° C., transferred into a separatory funnel containing 100 mL of water, and extracted three times with 100 mL of ethyl acetate. The organic layer was washed with water and dehydrated with anhydrous sodium sulfate. After the desiccant was filtered, the filtrate was concentrated, and the residue was purified through silica gel column chromatography to obtain 8.41 g of a compound represented by the following Formula (10) as a precursor compound.

[Chem. 15]

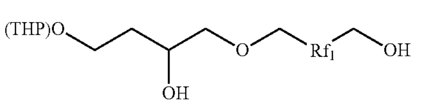

(10)

(in Formula (10), $Rf_1$ is the PFPE chain represented by Formula (4-1); in $Rf_1$, h indicating an average degree of polymerization represents 4.5 and i indicating an average degree of polymerization represents 4.5; and THP represents a tetrahydropyranyl group).

8.41 g of the compound represented by Formula (10) as the precursor compound obtained above, 0.88 g of epibromohydrin, and 10 mL of t-butanol were put into 100 mL eggplant flask under a nitrogen gas atmosphere, and stirred at room temperature until they became uniform. 0.96 g of potassium tert-butoxide was added to the uniform solution, and the mixture was stirred and reacted at 70° C. for 23 hours.

The reaction solution obtained after the reaction was returned to room temperature, transferred into a separatory funnel containing 100 ml of water, and extracted three times with 100 mL of ethyl acetate. The organic layer was washed with water and dehydrated with anhydrous sodium sulfate. After the desiccant was filtered, the filtrate was concentrated, and the residue was purified through silica gel column chromatography to obtain 5.61 g of a compound represented by the following Formula (11) as a first intermediate compound.

(in Formula (11), $Rf_1$ is the PFPE chain represented by Formula (4-1); in two $Rf_1$'s, h indicating an average degree of polymerization represents 4.5 and i indicating an average degree of polymerization represents 4.5; and THP represents a tetrahydropyranyl group).

(Second Reaction Step)

5.61 g of the compound represented by Formula (11) as the first intermediate compound obtained above, 4.18 g of the compound represented by Formula (8-1), and 20 mL of dimethylformamide were put into 100 mL eggplant flask under a nitrogen gas atmosphere, and stirred at room temperature until they became uniform. 0.85 g of sodium hydride was added to the uniform solution, and the mixture was stirred and reacted at 40° C. for 16 hours.

The reaction solution obtained after the reaction was returned to room temperature, 5 g of a 10% hydrogen chloride/methanol solution (hydrogen chloride-methanol reagent (5-10%), commercially available from Tokyo Chemical Industry Co., Ltd.) was added, and the mixture was stirred at room temperature for 4 hours. Then, the reaction solution was transferred little by little into a separatory funnel containing 100 mL of a saturated sodium bicarbonate solution, and extracted with twice with 200 mL of ethyl acetate. The organic layer was washed with 100 mL of a saline solution, 100 mL of a saturated sodium bicarbonate solution, and 100 mL of a saline solution in that order, and dehydrated with anhydrous sodium sulfate. After the desiccant was filtered, the filtrate was concentrated, and the residue was purified through silica gel column chromatography to obtain 2.45 g of a compound (N) (in Formula (N), $Rf_1$ is the PFPE chain represented by Formula (4-1), and in two $Rf_1$'s, h indicating an average degree of polymerization represents 4.5 and i indicating an average degree of polymerization represents 4.5).

The obtained compound (N) was subjected to $^1$H-NMR and $^{19}$F-NMR measurement, and the structure was identified based on the following results.

$^1$H-NMR (acetone-$D_6$): δ[ppm]=1.60-1.80 (4H), 3.40-3.85 (32H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

Example 15

The compound represented by Formula (O) was obtained by the following method.

2.68 g of the compound (O) (in Formula (O), $Rf_1$ is the PFPE chain represented by Formula (4-1), and in two $Rf_1$'s, h indicating an average degree of polymerization represents 4.5 and i indicating an average degree of polymerization represents 4.5) was obtained in the same operation as in Example 14 except that, in place of the compound represented by Formula (7-1), the compound represented by Formula (7-3) was used.

The obtained compound (O) was subjected to $^1$H-NMR and $^{19}$F-NMR measurement, and the structure was identified based on the following results.

$^1$H-NMR (acetone-$D_6$): δ[ppm]=3.40-3.85 (44H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

Example 16

The compound represented by Formula (P) was obtained by the following method.

2.64 g of the compound (P) (in Formula (P), $Rf_1$ is the PFPE chain represented by Formula (4-1), and in two $Rf_1$'s, h indicating an average degree of polymerization represents 4.5 and i indicating an average degree of polymerization represents 4.5) was obtained in the same operation as in Example 14 except that, in place of the compound represented by Formula (7-1), a compound represented by Formula (7-7) was used.

The obtained compound (P) was subjected to $^1$H-NMR and $^{19}$F-NMR measurement, and the structure was identified based on the following results.

$^1$H-NMR (acetone-$D_6$): δ[ppm]=1.60-1.80 (4H), 2.00-2.10 (4H), 3.40-3.85 (34H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

Example 17

The compound represented by Formula (Q) was obtained by the following 2.52 g of the compound (Q) (in Formula (Q), $Rf_1$ is the PFPE chain represented by Formula (4-1); and in two $Rf_1$'s, h indicating an average degree of polymerization represents 4.5 and i indicating an average degree of polymerization represents 4.5) was obtained in the same operation as in Example 14 except that, in place of the compound represented by Formula (8-1), a compound represented by Formula (8-2) was used.

The obtained compound (Q) was subjected to $^1$H-NMR and $^{19}$F-NMR measurement, and the structure was identified based on the following results.

$^1$H-NMR (acetone-$D_6$): δ[ppm]=1.60-1.80 (10H), 3.40-3.85 (32H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

Example 18

The compound represented by Formula (R) was obtained by the following method.

2.52 g of the compound (R) (in Formula (R), $Rf_1$ is the PFPE chain represented by Formula (4-1); and in two $Rf_1$'s, h indicating an average degree of polymerization represents 4.5 and i indicating an average degree of polymerization represents 4.5) was obtained in the same operation as in Example 14 except that, in place of the compound represented by Formula (8-1), the compound represented by Formula (8-4) was used.

The obtained compound (R) was subjected to $^1$H-NMR and $^{19}$F-NMR measurement, and the structure was identified based on the following results.

$^1$H-NMR (acetone-$D_6$): δ[ppm]=1.60-1.80 (4H), 3.40-3.85 (44H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

Example 19

The compound represented by Formula(S) was obtained by the following 2.18 g of the compound(S) (in Formula(S), $Rf_2$ is the PFPE chain represented by Formula (4-2); and in two $Rf_2$'s, j indicating an average degree of polymerization represents 4.5) was obtained in the same operation as in Example 14 except that, in place of the compound represented by $HOCH_2CF_2O(CF_2CF_2O)_i(CF_2O)_iCF_2CH_2OH$, a compound (a number-average molecular weight of 1,000 and a molecular weight distribution of 1.1) represented by $HOCH_2CF_2CF_2O(CF_2CF_2CF_2O)_jCF_2CF_2CH_2OH$ (in the formula, j indicating an average degree of polymerization is 4.5) was used.

The obtained compound(S) was subjected to $^1$H-NMR and $^{19}$F-NMR measurement, and the structure was identified based on the following results.

$^1$H-NMR (acetone-$D_6$): δ[ppm]=1.60-1.80 (4H), 3.40-3.85 (32H), 3.85-4.10 (8H)

$^{19}$F-NMR (acetone-$D_6$): δ[ppm]=−84.0 to −83.0 (36F), −86.4 (8F), −124.3 (8F), −130.0 to −129.0 (18F)

Example 20

The compound represented by Formula (T) was obtained by the following method.

(First Reaction Step)

In the same manner as in Example 14, as a precursor compound, a compound represented by Formula (10) was obtained.

Then, 7.81 g of a compound represented by the following Formula (13) was obtained as a first intermediate compound in the same operation as in Example 14 except that, in the reaction for obtaining a first intermediate compound in Example 14, in place of epibromohydrin, a compound represented by Formula (12) was used.

The compound represented by Formula (12) was synthesized by a method of reacting a compound (a number-average molecular weight of 1,000 and a molecular weight distribution of 1.1) represented by $HOCH_2CF_2O(CF_2CF_2O)$ n $(CF_2O)_iCF_2CH_2OH$ (in the formula, h indicating an average degree of polymerization is 4.5, and i indicating an average degree of polymerization is 4.5) with epibromohydrin.

[Chem. 17]

(12)

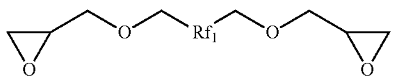

(in Formula (12), $Rf_1$ is the PFPE chain represented by Formula (4-1); and in $Rf_1$, h indicating an average degree of polymerization represents 4.5 and i indicating an average degree of polymerization represents 4.5).

[Chem. 18]

(13)

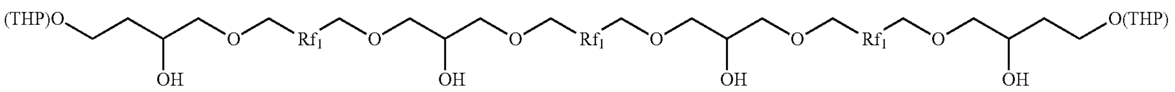

(in Formula (13), $Rf_1$ is the PFPE chain represented by Formula (4-1); in three $Rf_1$'s, h indicating an average degree of polymerization represents 4.5 and i indicating an average degree of polymerization represents 4.5; and THP represents a tetrahydropyranyl group).

(Second Reaction Step)

7.81 g of the compound represented by Formula (13) as the first intermediate compound obtained above, 6.32 g of the compound represented by Formula (8-1), and 20 mL of dimethylformamide were put into 100 mL eggplant flask under a nitrogen gas atmosphere, and stirred at room temperature until they became uniform. 1.08 g of sodium hydride was added to the uniform solution, and the mixture was stirred and reacted at 40° C. for 16 hours.

The reaction solution obtained after the reaction was returned to room temperature, and 5 g of a 10% hydrogen chloride/methanol solution (a hydrogen chloride-methanol reagent (5-10%), commercially available from Tokyo Chemical Industry Co., Ltd.) was added and the mixture was stirred at room temperature for 4 hours. Then, the reaction solution was transferred little by little into a separatory funnel containing 100 mL of a saturated sodium bicarbonate solution, and extracted with twice with 200 mL of ethyl acetate. The organic layer was washed with 100 mL of a saline solution, 100 mL of a saturated sodium bicarbonate solution, and 100 mL of a saline solution in that order, and dehydrated with anhydrous sodium sulfate. After the desiccant was filtered, the filtrate was concentrated, and the residue was purified through silica gel column chromatography to obtain 2.71 g of a compound (T) (in Formula (T), $Rf_1$ is the PFPE chain represented by Formula (4-1), and in three $Rf_1$'s, h indicating an average degree of polymerization represents 4.5 and i indicating an average degree of polymerization represents 4.5).

The obtained compound (T) was subjected to $^1$H-NMR and $^{19}$F-NMR measurement, and the structure was identified based on the following results.

$^1$H-NMR (acetone-$D_6$): δ[ppm]=1.60-1.80 (4H), 3.40-3.85 (42H), 3.85-4.10 (12H)

$^{19}$F-NMR (acetone-$D_6$): δ[ppm]=−55.5 to −51.5 (27F), −78.5 (6F), −80.5 (6F), −91.0 to −88.5 (54F)

Example 21

The compound represented by Formula (U) was obtained by the following method.

2.68 g of the compound (U) (in Formula (U), $Rf_1$ is the PFPE chain represented by Formula (4-1), and in three $Rf_1$'s, h indicating an average degree of polymerization represents 4.5 and i indicating an average degree of polymerization represents 4.5) was obtained in the same operation as in Example 20 except that, in place of the compound represented by Formula (7-1), a compound represented by Formula (7-3) was used.

The obtained compound (U) was subjected to $^1$H-NMR and $^{19}$F-NMR measurement, and the structure was identified based on the following results.

$^1$H-NMR (acetone-$D_6$): δ[ppm]=3.40-3.85 (54H), 3.85-4.10 (12H)

$^{19}$F-NMR (acetone-$D_6$): δ[ppm]=−55.5 to −51.5 (27F), −78.5 (6F), −80.5 (6F), −91.0 to −88.5 (54F)

Example 22

The compound represented by Formula (V) was obtained by the following 2.92 g of the compound (V) (in Formula (V), $Rf_1$ is the PFPE chain represented by Formula (4-1), and in three $Rf_1$'s, h indicating an average degree of polymerization represents 4.5 and i indicating an average degree of polymerization represents 4.5) was obtained in the same operation as in Example 20 except that, in place of the compound represented by Formula (7-1), a compound represented by Formula (7-7) was used.

The obtained compound (V) was subjected to $^1$H-NMR and $^{19}$F-NMR measurement, and the structure was identified based on the following results.

$^1$H-NMR (acetone-$D_6$): δ[ppm]=1.60-1.80 (4H), 2.00-2.10 (4H), 3.40-3.85 (44H), 3.85-4.10 (12H)

$^{19}$F-NMR (acetone-$D_6$): δ[ppm]=−55.5 to −51.5 (27F), −78.5 (6F), −80.5 (6F), −91.0 to −88.5 (54F)

Example 23

The compound represented by Formula (W) was obtained by the following method.

2.74 g of the compound (W) (in Formula (W), $Rf_1$ is the PFPE chain represented by Formula (4-1), and in three $Rf_1$'s, h indicating an average degree of polymerization represents 4.5 and i indicating an average degree of polymerization represents 4.5) was obtained in the same operation as in Example 20 except that, in place of the compound represented by Formula (8-1), the compound represented by Formula (8-4) was used.

The obtained compound (W) was subjected to $^{1}$H-NMR and $^{19}$F-NMR measurement, and the structure was identified based on the following results.

$^{1}$H-NMR (acetone-$D_6$): δ[ppm]=1.60-1.80 (4H), 3.40-3.85 (54H), 3.85-4.10 (12H)

$^{19}$F-NMR (acetone-$D_6$): δ[ppm]=−55.5 to −51.5 (27F), −78.5 (6F), −80.5 (6F), −91.0 to −88.5 (54F)

Example 24

The compound represented by Formula (X) was obtained by the following method.

2.58 g of the compound (X) (in Formula (X), $Rf_2$ is the PFPE chain represented by Formula (4-2); and in three $Rf_2$'s, j indicating an average degree of polymerization represents 4.5) was obtained in the same operation as in Example 20 except that, in place of the compound represented by $HOCH_2CF_2O(CF_2CF_2O)_i(CF_2O)_iCF_2CH_2OH$, a compound (a number-average molecular weight of 1,000 and a molecular weight distribution of 1.1) represented by $HOCH_2CF_2CF_2O(CF_2CF_2CF_2O)_iCF_2CF_2CH_2OH$ (in the formula, j indicating an average degree of polymerization is 4.5) was used.

The obtained compound (X) was subjected to $^{1}$H-NMR and $^{19}$F-NMR measurement, and the structure was identified based on the following results.

$^{1}$H-NMR (acetone-$D_6$): δ[ppm]=1.60-1.80 (4H), 3.40-3.85 (42H), 3.85-4.10 (12H)

$^{19}$F-NMR (acetone-$D_6$): [ppm]=−84.0 to −83.0 (54F), −86.4 (12F), −124.3 (12F), −130.0 to −129.0 (27F)

Example 25

The compound represented by Formula (XX) was obtained by the following 2.45 g of the compound (XX) (in Formula (XX), $Rf_1$ is the PFPE chain represented by Formula (4-1); and in two $Rf_1$'s, h indicating an average degree of polymerization represents 4.5 and i indicating an average degree of polymerization represents 4.5) was obtained in the same operation as in Example 14 except that, in place of the compound represented by Formula (7-1), the compound represented by Formula (7-2) was used.

The obtained compound (XX) was subjected to $^{1}$H-NMR and $^{19}$F-NMR measurement, and the structure was identified based on the following results.

$^{1}$H-NMR (acetone-$D_6$): δ[ppm]=3.40-3.85 (32H), 3.85-4.10 (8H)

$^{19}$F-NMR (acetone-$D_6$): δ[ppm]=−55.5 to −51.5 (18F), −78.5 (4F), −80.5 (4F), −91.0 to −88.5 (36F)

The values of x when the compounds (A) to (X), and (XX) of Examples 1 to 25 thus obtained were applied to Formula (1), and the structures of $R^1$, $R^2$, $R^3$, $R^4$, $R^5$, and $R^6$ are shown in Table 1 and Table 2.

TABLE 1

| Compound | x | $R^1$ | $R^2$ | $R^3$ | $R^4$ | $R^5$ | $R^6$ |
|---|---|---|---|---|---|---|---|
| (A) | 0 | (5-1) | (2-1) n1 = 2 | (4-1) | — | (2-3) n2 = 2 | (5-1) |
| (B) | 0 | (5-2) | (2-1) n1 = 2 | (4-1) | — | (2-3) n2 = 2 | (5-2) |
| (C) | 0 | (5-3) | (2-1) n1 = 2 | (4-1) | — | (2-3) n2 = 2 | (5-3) |
| (D) | 0 | (5-4) | (2-1) n1 = 2 | (4-1) | — | (2-3) n2 = 2 | (5-4) |
| (E) | 0 | (5-5) | (2-1) n1 = 2 | (4-1) | — | (2-3) n2 = 2 | (5-5) |
| (F) | 0 | (5-6) | (2-1) n1 = 2 | (4-1) | — | (2-3) n2 = 2 | (5-6) |
| (G) | 0 | (5-7) | (2-1) n1 = 2 | (4-1) | — | (2-3) n2 = 2 | (5-7) |
| (H) | 0 | (5-8) | (2-1) n1 = 2 | (4-1) | — | (2-3) n2 = 2 | (5-8) |
| (I) | 0 | (5-1) | (2-1) n1 = 3 | (4-1) | — | (2-3) n2 = 3 | (5-1) |
| (J) | 0 | (5-1) | (2-1) n1 = 4 | (4-1) | — | (2-3) n2 = 4 | (5-1) |
| (K) | 0 | (5-1) | (2-2) | (4-1) | — | (2-4) | (5-1) |
| (L) | 0 | (5-1) | (2-1) n1 = 2 | (4-2) | — | (2-3) n2 = 2 | (5-1) |
| (M) | 0 | (5-1) | (2-1) n1 = 2 | (4-3) | — | (2-3) n2 = 2 | (5-1) |

TABLE 2

| Compound | x | $R^1$ | $R^2$ | $R^3$ | $R^4$ | $R^5$ | $R^6$ |
|---|---|---|---|---|---|---|---|
| (N) | 1 | (5-1) | (2-1) n1 = 2 | (4-1) | (3-1) n3 = 2, y1 = 1, y2 = 1 | (2-3) n2 = 2 | (5-1) |
| (O) | 1 | (5-3) | (2-1) n1 = 2 | (4-1) | (3-1) n3 = 2, y1 = 1, y2 = 1 | (2-3) n2 = 2 | (5-3) |
| (P) | 1 | (5-7) | (2-1) n1 = 2 | (4-1) | (3-1) n3 = 2, y1 = 1, y2 = 1 | (2-3) n2 = 2 | (5-7) |
| (Q) | 1 | (5-1) | (2-1) n1 = 3 | (4-1) | (3-1) n3 = 3, y1 = 1, y2 = 1 | (2-3) n2 = 3 | (5-1) |
| (R) | 1 | (5-1) | (2-2) | (4-1) | (3-2) y3 = 1, y4 = 1 | (2-4) | (5-1) |
| (S) | 1 | (5-1) | (2-1) n1 = 2 | (4-2) | (3-1) n3 = 2, y1 = 1, y2 = 1 | (2-3) n2 = 2 | (5-1) |
| (T) | 2 | (5-1) | (2-1) n1 = 2 | (4-1) | (3-1) n3 = 2, y1 = 1, y2 = 1 | (2-3) n2 = 2 | (5-1) |

TABLE 2-continued

| Compound | x | $R^1$ | $R^2$ | $R^3$ | $R^4$ | $R^5$ | $R^6$ |
|---|---|---|---|---|---|---|---|
| (U) | 2 | (5-3) | (2-1) n1 = 2 | (4-1) | (3-1) n3 = 2, y1 = 1, y2 = 1 | (2-3) n2 = 2 | (5-3) |
| (V) | 2 | (5-7) | (2-1) n1 = 2 | (4-1) | (3-1) n3 = 2, y1 = 1, y2 = 1 | (2-3) n2 = 2 | (5-7) |
| (W) | 2 | (5-1) | (2-2) | (4-1) | (3-2) y3 = 1, y4 = 1 | (2-4) | (5-1) |
| (X) | 2 | (5-1) | (2-1) n1 = 2 | (4-2) | (3-1) n3 = 2, y1 = 1, y2 = 1 | (2-3) n2 = 2 | (5-1) |
| (XX) | 1 | (5-2) | (2-1) n1 = 2 | (4-1) | (3-1) n3 = 2, y1 = 1, y2 = 1 | (2-3) n2 = 2 | (5-2) |

Comparative Example 1

A compound represented by the following Formula (Y) was synthesized by the method described in Patent Document 1.

[Chem. 19]

(Y)

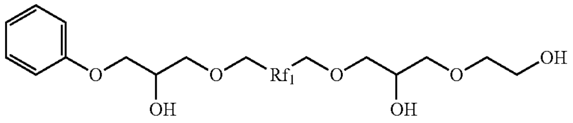

(in Formula (Y), $Rf_1$ is the PFPE chain represented by Formula (4-1); and in $Rf_1$, h indicating an average degree of polymerization represents 4.5 and i indicating an average degree of polymerization represents 4.5).

Comparative Example 2

A compound represented by the following Formula (Z) was synthesized by the method described in Patent Document 2.

[Chem. 20]

(Z)

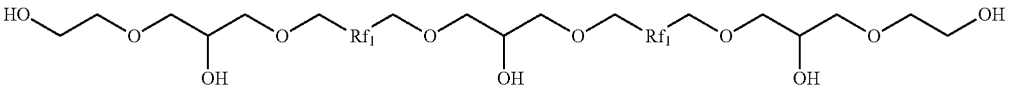

(in Formula (Z), $Rf_1$ is the PFPE chain represented by Formula (4-1); and in two $Rf_1$'s, h indicating an average degree of polymerization represents 4.5 and i indicating an average degree of polymerization represents 4.5).

Comparative Example 3

A compound represented by the following Formula (AA) was synthesized by the method described in Patent Document 3.

[Chem. 21]

(AA)

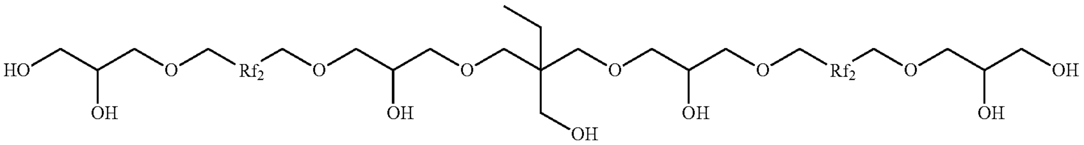

(in Formula (AA), $Rf_2$ is the PFPE chain represented by Formula (4-2); and in two $Rf_2$'s, j indicating an average degree of polymerization is 4.5).

Comparative Example 4

A compound represented by the following Formula (AB) was synthesized by the method described in Patent Document 3.

[Chem. 22]

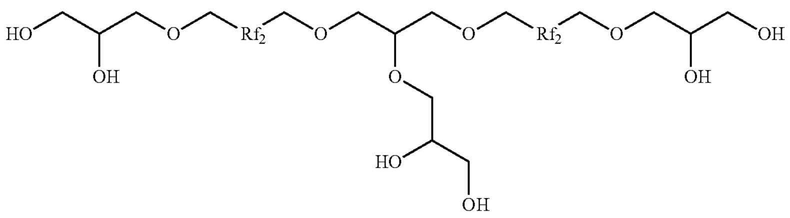

(AB)

(in Formula (AB), $Rf_2$ is the PFPE chain represented by Formula (4-2); and in two $Rf_2$'s, j indicating an average degree of polymerization is 4.5).

Comparative Example 5

A compound represented by the following Formula (AC) was synthesized by the method described in Patent Document 4.

[Chem. 23]

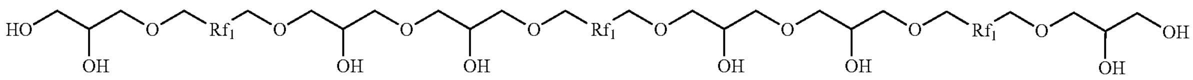

(AC)

(in Formula (AC), $Rf_1$ is the PFPE chain represented by Formula (4-1); and in three $Rf_1$ 's, h indicating an average degree of polymerization represents 7.0 and i indicating an average degree of polymerization represents 0).

Comparative Example 6

A compound represented by the following Formula (AD) was synthesized by the method described in Patent Document 5.

[Chem. 24]

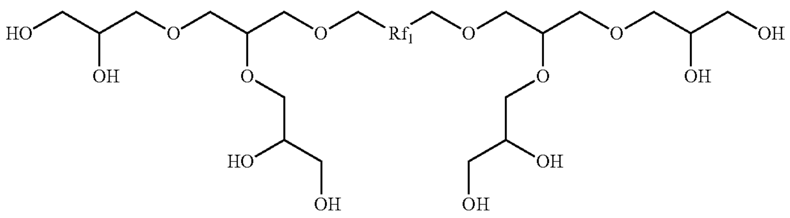

(AD)

(in Formula (AD), $Rf_1$ is the PFPE chain represented by Formula (4-1); and in $Rf_1$, h indicating an average degree of polymerization represents 4.5 and i indicating an average degree of polymerization represents 4.5).

Comparative Example 7

A compound represented by the following Formula (AE) was synthesized by the method described in Patent Document 5.

[Chem. 25]

(AE)

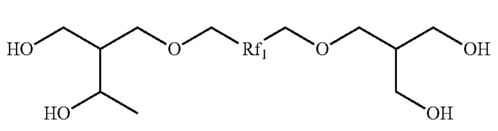

(in Formula (AE), $Rf_1$ is the PFPE chain represented by Formula (4-1); and in $Rf_1$, h indicating an average degree of polymerization represents 4.5 and i indicating an average degree of polymerization represents 4.5).

The number-average molecular weight (Mn) of the compounds of Examples 1 to 25 and Comparative Examples 1 to 7 thus obtained was measured by the method. The results are shown in Table 3 and Table 4.

Next, by the following method, lubricating layer forming solutions were prepared using the compounds obtained in Examples 1 to 25 and Comparative Examples 1 to 7. Then, lubricating layers of magnetic recording media were formed using the obtained lubricating layer forming solution by the following method, and magnetic recording media of Examples 1 to 25 and Comparative Examples 1 to 7 were obtained.

"Lubricating Layer Forming Solution"

The compounds obtained in Examples 1 to 25 and Comparative Examples 1 to 7 were each dissolved in Vertel (registered trademark) XF (product name, commercially available from Du Pont-Mitsui Fluorochemicals Co., Ltd.) as a fluorine-based solvent and diluted with Vertel XF so that the film thickness when applied onto the protective layer was 9.0 Å to 9.5 Å, and thereby a lubricating layer forming solution was obtained.

"Magnetic Recording Medium"

A magnetic recording medium in which an adhesive layer, a soft magnetic layer, a first base layer, a second base layer, a magnetic layer and a protective layer were sequentially provided on a substrate with a diameter of 65 mm was prepared. The protective layer was made of carbon.

The lubricating layer forming solutions of Examples 1 to 25 and Comparative Examples 1 to 7 were applied onto the protective layer of the magnetic recording medium in which respective layers up to the protective layer were formed by a dipping method. Here, the dipping method was performed under conditions of an immersion speed of 10 mm/sec, an immersion time of 30 sec, and a lifting speed of 1.2 mm/sec.

Then, the magnetic recording medium to which the lubricating layer forming solution was applied was put into a thermostatic chamber and subjected to a heat treatment at 120° C. for 10 minutes in order to remove the solvent in the lubricating layer forming solution and improve the adhesion between the protective layer and the lubricating layer, and thus a lubricating layer was formed on the protective layer to obtain a magnetic recording medium.

(Measurement of Film Thickness)

The film thickness of the lubricating layer of the magnetic recording media of Examples 1 to 25 and Comparative Examples 1 to 7 obtained in this manner was measured using FT-IR (product name: Nicolet iS50, commercially available from Thermo Fisher Scientific). The results are shown in Table 3 and Table 4.

Next, the magnetic recording media of Examples 1 to 25 and Comparative Examples 1 to 7 were subjected to the following chemical resistance test and pickup characteristic test.

[Chemical Resistance Test]

The contamination of the magnetic recording medium due to environmental substances that generated contamination substances under a high temperature environment was examined by the following method. Si ions were used as the environmental substance, and an amount of Si adsorbed was measured as the amount of the contamination substance that contaminated the magnetic recording medium generated from the environmental substance.

Specifically, the magnetic recording medium to be evaluated was held under a high temperature environment with a temperature of 85° C. and a humidity of 0% in the presence of siloxane-based Si rubber for 240 hours. Next, the amount of Si adsorbed present on the surface of the magnetic recording medium was analyzed and measured using secondary ion mass spectrometry (SIMS), and the degree of contamination with Si ions was evaluated as the amount of Si adsorbed. The amount of Si adsorbed was evaluated using a numerical value when the result of Comparative Example 1 was set as 1.00 based on the following evaluation criteria. The results are shown in Table 3 and Table 4.

"Evaluation Criteria"

◎ (excellent): the amount of Si adsorbed was less than 0.70 (the amount of Si adsorbed was very small)

O (good): the amount of Si adsorbed was 0.70 or more and less than 0.90 (the amount of Si adsorbed was small)

Δ (acceptable): the amount of Si adsorbed was 0.90 or more and less than 1.10 (the amount of Si adsorbed was large)

x (poor): the amount of Si adsorbed was 1.10 or more (the amount of Si adsorbed was very large)

[Pickup Characteristic Test]

A magnetic recording medium and a magnetic head were mounted on a spin stand, rotation was performed under a reduce pressure at room temperature (about 250 torr), and the magnetic head was floated from a fixed point for 10 minutes. Then, the surface of the magnetic head facing the magnetic recording medium was analyzed using an Electron Spectroscopy for Chemical Analysis (ESCA) analysis device. The intensity (signal intensity (a.u.)) of the fluorine-derived peak obtained by analysis using the ESCA analysis device indicated the amount of the lubricant adhered to the magnetic head. Using the obtained signal intensity, based on the following evaluation criteria, pickup characteristics were evaluated. The results are shown in Table 3 and Table 4.

"Evaluation criteria"

◎ (excellent): the signal intensity was 160 or less (very small adhesion amount)

O (good): the signal intensity was 161 to 300 (small adhesion amount)

Δ (acceptable): the signal intensity was 301 to 1,000 (large adhesion amount)

x (poor): the signal intensity was 1,001 or more (very large adhesion amount)

TABLE 3

| | Compound | Number-average molecular weight | Film thickness (Å) | Chemical resistance test | Pickup characteristic test |
|---|---|---|---|---|---|
| Example 1 | (A) | 1264 | 9.3 | ◎ | ◎ |
| Example 2 | (B) | 1239 | 9.2 | ◎ | ○ |
| Example 3 | (C) | 1326 | 9.4 | ◎ | ◎ |
| Example 4 | (D) | 1475 | 9.1 | ○ | ◎ |
| Example 5 | (E) | 1463 | 9.1 | ○ | ◎ |
| Example 6 | (F) | 1392 | 9.4 | ○ | ○ |
| Example 7 | (G) | 1364 | 9.2 | ◎ | ◎ |
| Example 8 | (H) | 1405 | 9.0 | ◎ | ◎ |
| Example 9 | (I) | 1280 | 9.2 | ◎ | ◎ |
| Example 10 | (J) | 1312 | 9.3 | ◎ | ◎ |
| Example 11 | (K) | 1350 | 9.5 | ◎ | ◎ |
| Example 12 | (L) | 1253 | 9.2 | ◎ | ◎ |
| Example 13 | (M) | 1271 | 9.2 | ◎ | ◎ |
| Example 14 | (N) | 2368 | 9.1 | ◎ | ◎ |
| Example 15 | (O) | 2431 | 9.4 | ◎ | ◎ |
| Example 16 | (P) | 2485 | 9.2 | ◎ | ◎ |
| Example 17 | (Q) | 2390 | 9.2 | ◎ | ◎ |
| Example 18 | (R) | 2451 | 9.3 | ◎ | ◎ |
| Example 19 | (S) | 2371 | 9.1 | ◎ | ◎ |
| Example 20 | (T) | 3464 | 9.0 | ◎ | ◎ |
| Example 21 | (U) | 3525 | 9.2 | ◎ | ◎ |
| Example 22 | (V) | 3572 | 9.0 | ◎ | ◎ |
| Example 23 | (W) | 3491 | 9.3 | ◎ | ◎ |
| Example 24 | (X) | 3550 | 9.3 | ◎ | ◎ |
| Example 25 | (XX) | 2344 | 9.4 | ◎ | ○ |

TABLE 4

| | Compound | Number-average molecular weight | Film thickness (Å) | Chemical resistance test | Pickup characteristic test |
|---|---|---|---|---|---|
| Comparative Example 1 | (Y) | 1265 | 9.1 | Δ | X |
| Comparative Example 2 | (Z) | 2302 | 9.5 | Δ | Δ |
| Comparative Example 3 | (AA) | 2391 | 9.3 | X | Δ |
| Comparative Example 4 | (AB) | 2277 | 9.2 | Δ | X |
| Comparative Example 5 | (AC) | 3406 | 9.4 | X | X |
| Comparative Example 6 | (AD) | 1403 | 9.5 | X | Δ |
| Comparative Example 7 | (AE) | 1174 | 9.5 | Δ | Δ |

As shown in Table 3, the magnetic recording media of Examples 1 to 25 each having a lubricating layer formed using any of compounds (A) to (X), and (XX) were all evaluated as ◎ (excellent) or O (good) in the chemical resistance test and the pickup characteristic test. Accordingly, it was confirmed that the lubricating layers of the magnetic recording media of Examples 1 to 25 had favorable chemical substance resistance and a strong pickup minimizing effect.

This was speculated to be because all of the compounds (A) to (X), and (XX) were the fluorine-containing ether compound represented by Formula (1). More specifically, it was speculated that, in the compounds (A) to (X), and (XX), none of $R^2$ arranged between the perfluoropolyether chain ($R^3$) and the terminal group ($R^1$), $R^5$ arranged between $R^3$ and the terminal group ($R^6$), and $R^4$ arranged between $R^3$'s when there were two or three $R^3$'s contained a secondary hydroxy group and all had a side chain moiety branching from the chain structure of the fluorine-containing ether compound and linked by an ether bond, and the side chain moiety had a primary hydroxy group arranged at the tip and had a linking group containing a methylene group ($—CH_2—$) that bonded a carbon atom to which a primary hydroxy group was bonded and an oxygen atom that was bonded to a carbon atom in the main chain moiety.

On the other hand, as shown in Table 4, Comparative Examples 1 to 7 each having a lubricating layer formed using any of the compounds (Y) to (AE) were all evaluated as Δ (acceptable) or x (poor) in the chemical resistance test and the pickup characteristic test.

This was speculated to be because, in Comparative Examples 1 to 6, the lubricating layer was formed using the compounds (Y) to (AD) in which a linking group arranged between the perfluoropolyether chain and the terminal group and/or a linking group arranged between perfluoropolyether chains contained a secondary hydroxy group.

In addition, in Comparative Example 7, the lubricating layer was formed using the compound (AE) containing no secondary hydroxy group. However, in the compound (AE), between the perfluoropolyether chain and the terminal group, there was no linking group containing a side chain moiety branching from the chain structure of the fluorine-containing ether compound and linked by an ether bond. More specifically, since two hydroxymethyl groups (—$CH_2OH$) arranged at both ends of the compound (AE) were not ether-bonded to tertiary carbon that formed the chain structure of the fluorine-containing ether compound, the flexibility was insufficient. In addition, in the compound (AE), two primary hydroxy groups arranged at both ends were bonded to tertiary carbon that formed the chain structure of the fluorine-containing ether compound via one methylene group. Therefore, in the compound (AE), the distance between tertiary carbon and two primary hydroxy groups arranged at both ends was close, and the movement of each of the two primary hydroxy groups was easily inhibited by the bulky tertiary carbon. Accordingly, it was speculated that, in Comparative Example 7 having a lubricating layer formed using the compound (AE), the fluidity around the primary hydroxy group in the compound (AE) was insufficient, the adsorption ability due to the interaction between the primary hydroxy group and the active sites on the protective layer was insufficient, and the evaluation results of the chemical resistance test and the pickup characteristic test were poor.

In addition, as shown in Table 3, among Examples 1 to 25, Examples 1 to 3, and 7 to 25 having a lubricating layer formed using the compounds (A) to (C), (G) to (X), and (XX) containing no secondary hydroxy group were all evaluated as ◎ (excellent) in the chemical resistance test and had very good results. Accordingly, it was confirmed that, when a compound not containing any secondary hydroxy group was used, a lubricating layer having better chemical substance resistance was obtained compared to when a compound containing secondary hydroxy groups in $R^1$ and $R^6$ was used.

In addition, as shown in Table 3, Examples 1 and 3 were all evaluated as ◎ (excellent) in the pickup characteristic test and had very good results. On the other hand, Example 2 was evaluated as O (good) in the pickup characteristic test.

This is because, in Examples 1 and 3, the compounds (A) and (C) in which the number of carbon atoms interposed between the hydroxy group contained in $R^1$ (=$R^6$) and tertiary carbon contained in $R^2$ (=$R^5$) was 2 or more were used, but in Example 2, the compound (B) in which the number of carbon atoms interposed between the hydroxy group contained in $R^1$ (=$R^6$) and tertiary carbon contained in $R^2$ (=$R^5$) was 1 was used. Due to this difference, in the compounds (A) and (C), compared to the compound (B), the distance between the hydroxy group contained in $R^1$ (=$R^6$) and $R^2$ (=$R^5$) was more appropriate. As a result, it was speculated that, in the compounds (A) and (C), compared to the compound (B), the movement of the primary hydroxy group contained in $R^1$ (=$R^6$) was less likely to be inhibited by the primary hydroxy group contained in $R^2$ (=$R^5$) and the bulky tertiary carbon contained in $R^2$ (=$R^5$).

In addition, as shown in Table 3, Examples 4 and 5 were all evaluated as ◎ (excellent) in the pickup characteristic test and had very good results. On the other hand, Example 6 was evaluated as O (good) in the pickup characteristic test. This is because, in Examples 4 and 5, the compounds (D) and (E) in which $R^1$ and $R^6$ had no rigid structure were used, but in Example 6, the compound (F) in which $R^1$ and $R^6$ contain a relatively rigid phenyl group was used. It was speculated that, due to this difference, in the compounds (D) and (E), compared to the compound (F), the movement of the hydroxy group contained in $R^1$ (=$R^6$) was less likely to be inhibited, and the hydroxy groups in $R^1$ and $R^6$ could move freely.

INDUSTRIAL APPLICABILITY

The present invention provides a fluorine-containing ether compound which can form a lubricating layer that has excellent chemical substance resistance and can minimize the occurrence of pickup.

When the lubricant for magnetic recording medium containing the fluorine-containing ether compound of the present invention is used, it is possible to form a lubricating layer having favorable chemical substance resistance and a strong pickup minimizing effect even if the thickness is thin.

REFERENCE SIGNS LIST

10 . . . Magnetic recording medium, 11 . . . Substrate, 12 . . . Adhesive layer, 13 . . . Soft magnetic layer, 14 . . . First base layer, 15 . . . Second base layer, 16 . . . Magnetic layer, 17 . . . Protective layer, 18 . . . Lubricating layer

The invention claimed is:

1. A fluorine-containing ether compound represented by the following Formula (1):

$$R^1—R^2—CH_2—R^3[-CH_2—R^4—CH_2—R^3]_x-CH_2—R^5—R^6 \quad (1)$$

(in Formula (1), $R^1$ and $R^6$ are each independently an organic group having 1 to 50 carbon atoms; $R^2$ is a divalent linking group represented by the following Formula (2-1) or (2-2); $R^5$ is a divalent linking group represented by the following Formula (2-3) or (2-4); x represents an integer of 0 to 2; $R^3$ is a perfluoropolyether chain; when x is 1 or 2, some or all of two or three $R^3$'s may be the same as or different from each other; $R^4$ is a divalent linking group represented by the following Formula (3-1) or (3-2); and when x is 2, two $R^4$'s may be the same as or different from each other)

[Chem. 1]

(2-1)

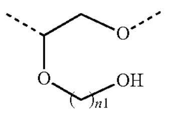

(2-2)

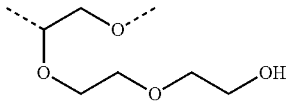

(2-3)

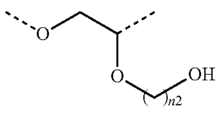

(2-4)

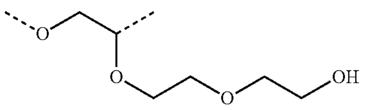

-continued (3-1)

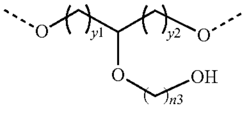

(3-2)

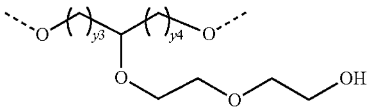

(in Formula (2-1), n1 represents an integer of 2 to 4; and in Formula (2-1), a dotted line bonded to a carbon atom indicates a bond that is bonded to $R^1$, and a dotted line bonded to an oxygen atom indicates a bond that is bonded to a methylene group)

(in Formula (2-2), a dotted line bonded to a carbon atom indicates a bond that is bonded to $R^1$, and a dotted line bonded to an oxygen atom indicates a bond that is bonded to a methylene group)

(in Formula (2-3), n2 represents an integer of 2 to 4; and in Formula (2-3), a dotted line bonded to a carbon atom indicates a bond that is bonded to $R^6$, and a dotted line bonded to an oxygen atom indicates a bond that is bonded to a methylene group)

(in Formula (2-4), a dotted line bonded to a carbon atom indicates a bond that is bonded to $R^6$, and a dotted line bonded to an oxygen atom indicates a bond that is bonded to a methylene group)

(in Formula (3-1), n3 represents an integer of 2 to 4; y1 represents an integer of 1 to 3; y2 represents an integer of 1 to 3; at least one of y1 and y2 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$)

(in Formula (3-2), y3 represents an integer of 1 to 3; y4 represents an integer of 1 to 3; at least one of y3 and y4 is 1; and a dotted line bonded to the oxygen atom on the left side indicates a bond that is bonded to the methylene group on the side of $R^1$, and a dotted line bonded to the oxygen atom on the right side indicates a bond that is bonded to the methylene group on the side of $R^6$).

2. The fluorine-containing ether compound according to claim 1, wherein, in Formula (1), $R^2$ is Formula (2-1) and $R^5$ is Formula (2-3), all x $R^4$'s are Formula (3-1), and in Formula (3-1), y1 is 1 and y2 is 1.

3. The fluorine-containing ether compound according to claim 2, wherein the values of n1 in Formula (2-1), n2 in Formula (2-3) and n3 in Formula (3-1) are all the same.

4. The fluorine-containing ether compound according to claim 1, wherein, in Formula (1), $R^2$ is Formula (2-2) and $R^5$ is Formula (2-4), all x $R^4$'s are Formula (3-2), and in Formula (3-2), y3 is 1 and y4 is 1.

5. The fluorine-containing ether compound according to claim 1, wherein, in Formula (1), $R^1$ and $R^6$ are each independently any of an organic group having a polar group, an organic group having a carbon-carbon unsaturated bond, and an organic group having both a polar group and a carbon-carbon unsaturated bond, wherein the polar group is at least one selected from the group consisting of a hydroxy group, an amino group, a carboxy group, a formyl group, a carbonyl group, a sulfo group, a cyano group, and a group having an amide bond, and wherein the carbon-carbon unsaturated bond is at least one selected from the group consisting of an optionally substituted aromatic hydrocarbon group, an unsaturated heterocyclic group, an alkenyl group, and an alkynyl group.

6. The fluorine-containing ether compound according to claim 1, wherein a total number of polar groups contained in $R^1$ and $R^6$ in Formula (1) is 1 to 4.

7. The fluorine-containing ether compound according to claim 1, wherein, in Formula (1), $R^1$—$R^2$— and $R^6$—$R^5$— are the same.

8. The fluorine-containing ether compound according to claim 1, wherein (x+1) $R^3$'s in Formula (1) are each independently a perfluoropolyether chain represented by the following Formula (4):

$$—(CF_2)_{w1}—O—(CF_2O)_{w2}—(CF_2CF_2O)_{w3}—(CF_2CF_2CF_2O)_{w4}—(CF_2CF_2CF_2CF_2O)_{w5}—(CF_2)_{w6}— \quad (4)$$

(in Formula (4), w2, w3, w4, and w5 indicate an average degree of polymerization and each independently represent 0 to 20; provided that all of w2, w3, w4, and w5 are not 0 at the same time; w1 and w6 are an average value representing the number of $CF_2$'s and each independently represent 1 to 3; and the arrangement order of repeating units ($CF_2O$), ($CF_2CF_2O$), ($CF_2CF_2CF_2O$), and ($CF_2CF_2CF_2CF_2O$) in Formula (4) is not particularly limited).

9. The fluorine-containing ether compound according to claim 1, wherein (x+1) $R^3$'s in Formula (1) are each independently any one selected from among perfluoropolyether chains represented by the following Formulae (4-1) to (4-4):

$$—CF_2—(OCF_2CF_2)_h—(OCF_2)_i—OCF_2— \quad (4\text{-}1)$$

(in Formula (4-1), h and i indicate an average degree of polymerization, h represents 1 to 20, and i represents 0 to 20)

$$—CF_2CF_2—(OCF_2CF_2CF_2)_j—OCF_2CF_2— \quad (4\text{-}2)$$

(in Formula (4-2), j indicates an average degree of polymerization and represents 1 to 15)

(4-3)

$$—CF_2CF_2CF_2—(OCF_2CF_2CF_2CF_2)_k—OCF_2CF_2CF_2—$$

(in Formula (4-3), k indicates an average degree of polymerization and represents 1 to 10)

(4-4)

$$—(CF_2)_{w7}—O—(CF_2CF_2CF_2O)_{w8}—(CF_2CF_2O)_{w9}—(CF_2)_{w10}—$$

(in Formula (4-4), w8 and w9 indicate an average degree of polymerization and each independently represent 1 to 20; and w7 and w10 are an average value representing the number of $CF_2$'s and each independently represent 1 to 2).

10. The fluorine-containing ether compound according to claim 1, wherein the number-average molecular weight is in a range of 500 to 10,000.

11. A lubricant for magnetic recording medium comprising the fluorine-containing ether compound according to claim 1.

12. A magnetic recording medium in which at least a magnetic layer, a protective layer, and a lubricating layer are sequentially provided on a substrate, wherein the lubricating layer contains the fluorine-containing ether compound according to claim 1.

13. The magnetic recording medium according to claim 12, wherein the average film thickness of the lubricating layer is 0.5 nm to 2.0 nm.

* * * * *